United States Patent
Nagai et al.

(10) Patent No.: US 8,373,156 B2
(45) Date of Patent: Feb. 12, 2013

(54) BIOLOGICAL COMPONENT DETECTION DEVICE

(75) Inventors: Youichi Nagai, Osaka (JP); Yasuhiro Iguchi, Osaka (JP)

(73) Assignee: Sumitomo Electric Industries, Ltd., Osaka (JP)

( * ) Notice: Subject to any disclaimer, the term of this patent is extended or adjusted under 35 U.S.C. 154(b) by 120 days.

(21) Appl. No.: 13/122,926

(22) PCT Filed: Jul. 30, 2009

(86) PCT No.: PCT/JP2009/063580
§ 371 (c)(1),
(2), (4) Date: Apr. 6, 2011

(87) PCT Pub. No.: WO2010/073769
PCT Pub. Date: Jul. 1, 2010

(65) Prior Publication Data
US 2012/0032147 A1 Feb. 9, 2012

(30) Foreign Application Priority Data
Dec. 22, 2008 (JP) ................... 2008-326276

(51) Int. Cl.
*H01L 29/06* (2006.01)
*H01L 31/0232* (2006.01)
*H01L 31/102* (2006.01)

(52) U.S. Cl. .......... 257/22; 257/14; 257/21; 257/102; 257/184; 257/188; 257/189; 257/431; 257/461; 257/463; 257/611; 257/615; 257/E29.005; 257/E29.022

(58) Field of Classification Search .............. 257/14, 257/21, 102, 184, 188, 189, 431, 436, 461, 257/463, 611, 615, E29.005, E29.022
See application file for complete search history.

(56) References Cited

U.S. PATENT DOCUMENTS
6,518,638 B1 * 2/2003 Kuhara et al. ............. 257/431
6,521,968 B2 * 2/2003 Kuhara et al. ............. 257/461
(Continued)

FOREIGN PATENT DOCUMENTS
JP 63-01079 1/1988
JP 03-38887 2/1991
(Continued)

OTHER PUBLICATIONS

Yamamoto et al., "Optical properties of $GaAs_{0.5}Sb_{0.5}$ and $In_{0.53}Ga_{0.47}As/GaAs_{0.5}Sb_{0.5}$ type II single hetero-structures lattice-matched to InP substrates grown by molecular beam epitaxy," J. of Crystal Growth, Elsevier 201/202, pp. 872-876 (1999).

(Continued)

*Primary Examiner* — Cheung Lee
*Assistant Examiner* — Jeremy Joy
(74) *Attorney, Agent, or Firm* — Fish & Richardson P.C.

(57) ABSTRACT

Provided is a biological component detection device with which a biological component can be detected at high sensitivity by using an InP-based photodiode in which a dark current is reduced without using a cooling mechanism and the sensitivity is extended to a wavelength of 1.8 μm or more. An absorption layer 3 has a multiple quantum well structure composed of group III-V semiconductors, a pn-junction 15 is formed by selectively diffusing an impurity element in the absorption layer, and the concentration of the impurity element in the absorption layer is $5 \times 10^{16}/cm^3$ or less, the diffusion concentration distribution control layer has an n-type impurity concentration of $2 \times 10^{15}/cm^3$ or less before the diffusion, the diffusion concentration distribution control layer having a portion adjacent to the absorption layer, the portion having a low impurity concentration. The biological component detection device is characterized in that an examination is conducted by receiving light having at least one wavelength of 3 μm or less, the wavelength being included in an absorption band of the biological component.

13 Claims, 16 Drawing Sheets

U.S. PATENT DOCUMENTS

| | | | |
|---|---|---|---|
| 8,198,623 B2 * | 6/2012 | Akita et al. | 257/14 |
| 2007/0096236 A1 * | 5/2007 | Yagyu et al. | 257/438 |
| 2008/0142714 A1 | 6/2008 | Nagai et al. | |
| 2009/0001412 A1 * | 1/2009 | Nagai et al. | 257/184 |
| 2010/0051905 A1 * | 3/2010 | Iguchi et al. | 257/14 |

FOREIGN PATENT DOCUMENTS

| | | |
|---|---|---|
| JP | 05-160426 | 6/1993 |
| JP | 05-160429 | 6/1993 |
| JP | 09-219563 | 8/1997 |
| JP | 10-118108 | 5/1998 |
| JP | 11-128209 | 5/1999 |
| JP | 11-216131 | 8/1999 |
| JP | 2001-095806 | 4/2001 |
| JP | 2001-144278 | 5/2001 |
| JP | 2002-065645 | 5/2002 |
| JP | 2002-373999 | 12/2002 |
| JP | 2005-083901 | 3/2005 |
| JP | 2005-519682 | 7/2005 |
| JP | 2006-270060 | 10/2006 |
| JP | 2007-80920 | 3/2007 |
| JP | 2007-201432 | 8/2007 |
| JP | 2007-324572 | 12/2007 |
| JP | 2008-153311 | 7/2008 |
| JP | 2008-171885 | 7/2008 |
| JP | 2008-205001 | 9/2008 |
| JP | 2008-270760 | 11/2008 |
| JP | 2008-288293 | 11/2008 |
| WO | 2007/120931 | 10/2007 |

OTHER PUBLICATIONS

Sidhu et al., "A Long-Wavelength Photodiode on InP Using Lattice Matched GaInAs-GaAsSb Type-II Quantum Wells," IEEE Photonics Tech. Letters 17(12):2715-2717 (2005).

Nakayama, M., "Technology trend of infrared detectors," Sensor Technology, 9(3): 1-64 (Mar. 1989).

Kawano, S. (ed.), "Applications of near-infrared spectroscopy to foods" in Handbook of nondestructive measurement for foods, Science Forum, Ch. 3 and 4, pp. 33-40 (2003).

International Search Report for PCT/JP2009/063580, Nov. 2, 2009.

* cited by examiner

NOTE: SWIR COSMIC LIGHT IS REPRESENTED BY ARBITRARY SCALE

BIOLOGICAL COMPONENT DETECTION DEVICE

TECHNICAL FIELD

The present invention relates to a biological component detection device including a semiconductor light-receiving element having sensitivity to light in the near-infrared region.

BACKGROUND ART

Biological components such as the blood and body fat of humans and the like have absorption bands in the near-infrared region, and thus near-infrared spectroscopy has attracted attention as a noninvasive analytical method, and studies and practical applications thereof have been intensively implemented. In particular, recently, diabetes, obesity etc. have been focused on, and absorption spectrum bands of glucose, which is the main component of blood sugar, cholesterol, lipids, and the like lie in the near-infrared region. Thus, studies using the skin of a biological body or the like have been actively performed. In analysis by near-infrared spectroscopy, an output signal includes necessary information and a large amount of noise due to a light-receiving element. Consequently, in order to extract necessary information regarding an output signal without totally depending on an improvement of the performance of sensors (light-receiving elements), a spectroscopic method, chemometrics, or the like has been used as an important method.

In the near-infrared region, the above-mentioned sensors (light-receiving elements) are broadly divided into electron tubes and photodiodes (PDs) which are solid-state components. Among these sensors, PDs have a small size and can be easily highly integrated to form a one-dimensional array, a two-dimensional array, or the like, and thus research and development of PDs has been widely performed (Non-Patent Document 1). The present invention targets a detection device for biological components, the detection device including a PD. Currently, the following PDs or PD arrays are used.

(1) An example such PDs or PD arrays is PDs or arrays thereof having sensitivity up to the infrared region and also having sensitivity in the near-infrared region. Specific examples of such PDs include germanium (Ge)-based PDs, lead sulfide (PbS)-based PDs, HgCdTe-based PDs, one-dimensional arrays thereof, and two-dimensional arrays thereof.

(2) Another example of such PDs or PD arrays is InP-based PDs having sensitivity at a wavelength of 1.7 μm or less in the near-infrared region, InGaAs-based PDs included in the category of the InP-based PDs, and arrays thereof. Herein, the InP-based PDs refer to PDs including an absorption layer composed of a group III-V compound semiconductor and provided on an InP substrate, and InGaAs-based PDs are also included in the InP-based PDs.

Among the above photodiodes, photodiodes described in (1) are often cooled in order to reduce noise. For example, most of the photodiodes are operated under cooling at the liquid nitrogen temperature (77 K) or under cooling with a Peltier device. Accordingly, devices including such photodiodes have a large size, and the device cost is increased. Although such devices can be used at room temperature, the devices have a problem that a dark current is large in the wavelength range of 2.5 μm or less and the detection capability is poor. On the other hand, the InP-base PDs described in (2) have the following disadvantages: (I) In InGaAs, which is lattice-matched to InP, although a dark current is low, the sensitivity of the PD is limited to a wavelength range of 1.7 μm or less in the near-infrared region. (II) In extended-InGaAs, in which the wavelength region where light can be received is extended to 2.6 μm, the dark current is large, and cooling is necessary. Accordingly, in the InP-based PDs, light having a wavelength of 2.0 μm or more, which is important in examinations of biological components, cannot be used or it is necessary to cool the PDs in order to use the light.

In biological component detection using near-infrared light, detection targeting the blood sugar level (such as glucose and grape sugar), which is directly related to diabetes, is most commonly performed (Patent Documents 1 to 4), and next most commonly performed is detection of body fat (Patent Document 5). Furthermore, from the cosmetic standpoint, measurement of collagen related to wrinkles of the skin has been performed using near-infrared light (Patent Document 6). In addition, with regard to a distribution of collagen and the like during a surgery of the cornea, a measurement of infrared rays has been proposed (Patent Document 7).

In the above-mentioned biological component detection, a single element or an array of elements of InGaAs, PbS, Ge, HgCdTe, an extended-InGaAs including multistage step buffer layers, or the like is used in a spectroscopic device for near-infrared light. A light-receiving wavelength range common to all the above-mentioned biological component detection devices is 1 to 1.8 μm. However, some of the devices determine the upper limit of the light-receiving wavelength range to about 2.0 μm or 2.5 μm.

As described above, as for InGaAs, it is necessary to extend the sensitivity to the long-wavelength side of the near-infrared region. To improve the sensitivity, the methods below have been proposed.

(K1) The indium (In) proportion of an InGaAs absorption layer is increased, and lattice mismatching between the absorption layer and an InP substrate is absorbed by interposing step buffer layers, in which the In proportion is changed stepwise, therebetween (Patent Document 8).

(K2) Nitrogen (N) is incorporated in an InGaAs absorption layer to form a GaInNAs absorption layer (Patent Document 9). Lattice matching with an InP substrate is satisfied by incorporating a large amount of N.

(K3) An extension of the light-receiving wavelength range to the long-wavelength side is realized by providing a type-II multiple quantum well structure composed of GaAsSb and InGaAs (Non-Patent Document 2). Lattice matching with an InP substrate is satisfied.

(K4) Formation of a two-dimensional array is realized by forming element separation trenches between light-receiving elements (pixels) by wet etching (Patent Document 10).

Non-Patent Document 1: Masao Nakayama "Technology trend of infrared detectors" Sensor Technology, 1989 March issue (Vol. 9, No. 3), p. 61-64

Non-Patent Document 2: R. Sidhu, "A Long-Wavelength Photodiode on InP Using Lattice-Matched GaInAs—GaAsSb Type-II Quantum Wells, IEEE Photonics Technology Letters, Vol. 17, No. 12 (2005), pp. 2715-2717

Patent Document 1: Japanese Unexamined Patent Application Publication No. 2002-065645

Patent Document 2: Japanese Unexamined Patent Application Publication No. 11-216131

Patent Document 3: Japanese Unexamined Patent Application Publication (Translation of PCT Application) No. 2005-519682

Patent Document 4: Japanese Unexamined Patent Application Publication No. 11-128209

Patent Document 5: Japanese Unexamined Patent Application Publication No. 2001-95806

Patent Document 6: Japanese Unexamined Patent Application Publication No. 2005-83901
Patent Document 7: Japanese Unexamined Patent Application Publication No. 10-118108
Patent Document 8: Japanese Unexamined Patent Application Publication No. 2002-373999
Patent Document 9: Japanese Unexamined Patent Application Publication No. 9-219563
Patent Document 10: Japanese Unexamined Patent Application Publication No. 2001-144278

DISCLOSURE OF INVENTION

Problems to be Solved by the Invention

In the biological component detection devices described above, in summary, structures have been proposed in which near-infrared light having a wavelength up to a maximum of 2.5 μm is used (Patent Documents 1 to 6). The upper limit of the wavelength is preferably large so long as the sensitivity is good because a large amount of information can be obtained. However, in order to receive light in a range exceeding a wavelength of 1.7 μm, as described above, the light-receiving element including PbS, HgCdTe, or the like has problems of a large dark current, a low detection capability, and a need for enhancing the detection resolution. When such a light-receiving element is used under cooling in order to enhance the detection capability, the biological component detection device has a large size, and the power consumption also increases.

Although an InGaAs light-receiving element that is lattice-matched to an InP substrate is excellent in terms of detection capability, the wavelength corresponding to the sensitivity of the element is 1.7 μm or less. Accordingly, this light-receiving element is not suitable for detecting biological components, which have a large number of absorption spectra in a wavelength range longer than this. In particular, as in a biological object, in the case where a large number of biological components together form biological tissue, in order to improve the resolution, it is desirable to comprehensively detect a biological component, which is a detection target, using two or more absorption bands attributable to the biological component. However, in such a detection of a biological component using two or more absorption bands, a sensitivity wavelength range of 1.7 μm or less is very insufficient.

Meanwhile, as described in (K1) to (K4) above, there are some candidates for a light-receiving element and a light-receiving element array that do not require cooling and that have sensitivity at the long-wavelength side of the near-infrared region. However, the candidates each have the following problems.

(K1): Since the InP substrate and the absorption layer are not completely lattice-matched to each other, a dark current due to a high lattice defect density is very high. Accordingly, a sufficiently high dynamic range (S/N ratio) cannot be achieved, and noise is high. Consequently, the number of dark spots (image omissions) increases.

In addition, in order to realize lattice matching, InP cannot be used as a window layer constituting a top layer of a laminate, and it is necessary to provide an InAsP window layer. Consequently, the sensitivity from the near-infrared region to the shorter wavelength side, in which important absorption bands are located in some biological components, decreases.

(K2): When the amount of N is about 10 atomic percent in order to extend the bandgap wavelength to the longer wavelength side while achieving lattice matching to InP, it is very difficult to obtain GaInNAs composed of good crystals. Furthermore, it is very difficult and almost impossible to obtain GaInNAs having a thickness of about 2 μm in order to sufficiently increase the sensitivity. In short, sharp images cannot be obtained.

(K3): When an impurity is introduced into an absorption layer having a multiple quantum well structure by an ordinary method, the crystal quality of the multiple quantum well structure is degraded. Therefore, the production yield decreases, thereby increasing the product cost, and a good crystal quality is not easily obtained. Accordingly, although the light-receiving wavelength range can be extended to a longer wavelength of about 2.5 μm, sharp images cannot be obtained.

(K4): In order to form an array by means of element separation by wet etching, it is necessary that an etchant enter trenches sufficiently deeply and uniformly. However, the etchant does not enter the trenches sufficiently deeply and uniformly and such a control is difficult. Consequently, the production yield decreases.

On the other hand, when dry etching is employed, light-receiving elements are damaged. In particular, in the case of a device that receives light diffracted in accordance with the wavelength, e.g., a biological component detection device, the above damage cannot be accepted.

If near-infrared spectroscopy can be easily performed with high sensitivity using a photodiode in which the dark current is suppressed without using a cooling mechanism, useful information about biological components can be routinely obtained, thereby accelerating the development of many fields related to healthcare, treatment of diseases, and the like.

An object of the present invention is to provide a biological component detection device which can detect a biological component with high sensitivity by using an InP-based photodiode in which the dark current is reduced without providing a cooling mechanism and the sensitivity is extended to a wavelength of 1.8 μm or more.

Means for Solving the Problems

A biological component detection device of the present invention is a device for detecting a component of a biological object using light in the near-infrared region. This device includes a light-receiving element composed of III-V group semiconductor, that receives light in the near-infrared region. The light-receiving element includes an absorption layer formed on an InP substrate and having a multiple quantum well structure, and the absorption layer has a bandgap wavelength of 1.8 μm or more and 3 μm or less. This device further includes a diffusion concentration distribution control layer made of III-V group semiconductor is disposed in contact with the absorption layer on a surface side of the absorption layer, the surface side being opposite to the InP substrate, and the diffusion concentration distribution control layer has a bandgap energy smaller than that of InP. In the light-receiving element, a pn-junction is formed by selectively diffusing an impurity element through the diffusion concentration distribution control layer so as to reach the absorption layer, the concentration of the impurity element in the absorption layer is $5 \times 10^{16}/cm^3$ or less, the diffusion concentration distribution control layer has an n-type impurity concentration of $2 \times 10^{15}/cm^3$ or less before the diffusion, the diffusion concentration distribution control layer having a portion adjacent to the absorption layer, the portion having a low impurity concentration, and the detection is performed by receiving, with the light-receiving element, light having at least one wavelength of 3 μm or less, the light constituting light transmitted through or reflected from the biological object.

According to the above configuration, by lowering the concentration of the impurity element to be $5\times10^{16}$ cm$^{-3}$ or less, a multiple quantum well structure having a bandgap energy corresponding to the near-infrared region can be formed without breaking the multiple quantum well structure, that is, without impairing the crystal quality. Furthermore, the impurity for forming the pn-junction of the light-receiving element is selectively diffused, that is, the impurity is introduced into the inside of the peripheral portion of the light-receiving element by diffusion so that the diffusion in the peripheral portion is two-dimensionally limited. Thus, the impurity is introduced so that the light-receiving elements are separated from each other. Accordingly, each of the light-receiving elements can be easily formed with high accuracy, and element separation trenches need not be provided. Thus, light-receiving elements having a low dark current can be formed. Consequently, light can be received at high sensitivity without cooling in a wavelength of 3 μm or less. There are several absorption bands of a biological component (molecule) in a wavelength range of 0.9 to 3 μm. Therefore, detection can be performed with the above biological component detection device using these plurality of absorption bands at the same time. Thus, the detection accuracy can be improved.

By controlling the bandgap of the diffusion concentration distribution control layer to be smaller than that of InP, even when the concentration of the impurity element in a thickness range at the absorption layer side of the diffusion concentration distribution control layer is decreased, the electrical resistance can be suppressed to be low. Thus, a decrease in the response time can be prevented. More specifically, the reasons why the bandgap of the diffusion concentration distribution control layer is controlled to be smaller than the bandgap of the InP substrate are as follows:

(1) When an absorption layer for the near-infrared region is formed of group III-V compound semiconductors, a material having a bandgap energy larger than the bandgap energy of the absorption layer is used as a window layer in some cases. In such a case, the same material as the semiconductor substrate is often used as the window layer in consideration of a lattice matching property and the like. It is assumed that the bandgap energy of the diffusion concentration distribution control layer is smaller than the bandgap energy of the window layer and larger than the bandgap energy of the absorption layer. This is because, if the bandgap energy of the diffusion concentration distribution control layer is smaller than the bandgap energy of the absorption layer and a structure in which the top surface of an epitaxial layer functions as an incident surface is adopted, the diffusion concentration distribution control layer absorbs light that should be absorbed by the absorption layer, thereby decreasing sensitivity of the absorption layer.

(2) By using a material having a bandgap energy smaller than a large bandgap energy of a material that is usually used as a window layer, even when the impurity concentration is reduced, it is possible to suppress an increase in the electrical resistance or a decrease in the electrical conductivity. As a result, as described above, a decrease in a response time can be suppressed in a voltage-applied state.

Here, the "detection" may refer to that a calibration curve of a predetermined component (a relationship between the concentration of the predetermined component and the intensity or the absorbance of light at the wavelength) is prepared in advance, and the concentration or the content of the predetermined component is determined. Alternatively, the "detection" may refer to a method in which such a calibration curve is not used. Note that the above pn-junction should be broadly interpreted as follows. In the absorption layer, when a region on a surface side opposite a surface from which the impurity element is introduced by selective diffusion is an impurity region (also referred to as "i region") in which the impurity concentration is low enough for the impurity region to be considered as an intrinsic semiconductor, a junction formed between this i-region and the impurity region formed by the selective diffusion is also included in the pn-junction. That is, the pn-junction mentioned above may be a pi-junction, an ni-junction, or the like. Furthermore, the pn-junction also includes the case where the p concentration in the pi-junction or the n concentration in the ni-junction is very low.

The diffusion concentration distribution control layer has a first region located adjacent to a surface of the diffusion concentration distribution control layer opposite the surface in contact with the absorption layer, the concentration of the impurity element in the first region being about $1\times10^{18}$/cm$^3$ or more, a second region located adjacent to the absorption layer, the concentration of the impurity element in the second region being $2\times10^{16}$/cm$^3$ or less, and a third region located between the first region and the second region, the third region having a smaller thickness than those of the first and second regions, and the concentration of the impurity element in the third region being more than $2\times10^{16}$/cm$^3$ and less than $1\times10^{18}$/cm$^3$.

In this case, a good crystal quality of the multiple quantum well structure can be ensured while reducing the interface resistance of an electrode disposed on the top surface side or allowing an ohmic contact of the electrode to be formed. The problem of an increase in the electrical resistance or a decrease in the electrical conductivity due to a low impurity concentration in a portion in the diffusion concentration distribution control layer can be reduced by controlling the bandgap energy of the diffusion concentration distribution control layer to be smaller than the bandgap energy corresponding to that of InP, as described above.

The absorption layer may have a type II quantum well structure. In this case, in absorption of electromagnetic waves, transition of electrons from a layer of a high valence band to a layer of a low conduction band can be performed. Thus, sensitivity to light in the longer wavelength range can be easily obtained.

The absorption layer may have a multiple quantum well structure composed of (InGaAs/GaAsSb) or a multiple quantum well structure composed of (GaInNAs (P, Sb)/GaAsSb). Herein, (GaInNAs (P, Sb)/GaAsSb) means (GaInNAsP/GaAsSb), (GaInNAsSb)/GaAsSb), (GaInNAsPSb)/GaAsSb), or (GaInNAs/GaAsSb). In this case, a light-receiving element having a good crystal quality and a low dark current can be easily obtained by using materials and techniques that have been accumulated to date.

The InP substrate may be an off-angle substrate which is tilted at 5° to 20° from (100) in the [111] direction or the [11-1] direction. In this case, it is possible to obtain a laminate including an absorption layer having a multiple quantum well structure in which the defect density is low and which has a good crystal quality. Consequently, it is possible to obtain a light-receiving element array or detection device in which a dark current is suppressed and the number of dark spots is small.

The impurity element may be zinc (Zn), and the diffusion concentration distribution control layer may be composed of InGaAs. In this case, the diffusion concentration distribution control layer can be formed of a material for which the dependency of the electrical resistance on the impurity concentration is small, the material having an electrical resistance which does not significantly increase even at a low impurity concentration. Suppressing an increase in the electrical resistance prevents the degradation of the response time. In addition, zinc used as the impurity has been widely used in selective diffusion to date, and can form a diffusion region with high accuracy. Accordingly, it is possible to prevent an increase in the electrical resistance on the lower side of the diffusion concentration distribution control layer while the impurity concentration which is high at the upper side, i.e., the diffusion introduction side is decreased toward the lower side, i.e., the absorption layer side in the diffusion concentration distribution control layer. Therefore, it is possible to prevent a region having a high impurity concentration from being formed in the absorption layer having a quantum well structure. As a result, a light-receiving element having a quantum well structure with a good crystal quality can be obtained without decreasing responsiveness. Note that the bandgap energy of InGaAs is 0.75 eV.

An InP window layer may be provided on the diffusion concentration distribution control layer. The formation of the window layer composed of InP does not decrease the crystal quality of the semiconductor stacked structure disposed inside. Accordingly, when a structure in which an epitaxial layer is disposed on the incident surface side is adopted, the InP window layer also effectively acts to suppress the dark current while preventing, for example, absorption of near-infrared light at a position closer to the incident side than the absorption layer. Furthermore, techniques for forming a passivation film on a crystal surface of InP have been accumulated and technically established, as compared with techniques for forming a passivation film on other crystal surfaces, for example, techniques for forming a passivation film on a surface of InGaAs. Accordingly, a current leakage on the surface can be easily suppressed.

In any two of the InP substrate, respective layers constituting the quantum well structure of the absorption layer, the diffusion concentration distribution control layer, and the InP window layer, a degree of lattice matching ($|\Delta a/a|$: where a represents a lattice constant and $\Delta a$ represents a difference in the lattice constant between the two) may be 0.002 or less. With this configuration, an absorption layer having a good crystal quality can be obtained by using an InP substrate that is commonly available. Accordingly, in a light-receiving element or light-receiving element array of near-infrared light having a wavelength of 1.8 µm or more, the dark current can be significantly suppressed.

The light-receiving element may have a structure in which a plurality of the light-receiving elements are one-dimensionally or two-dimensionally arrayed. In the light-receiving element array, a plurality of the light-receiving elements include a semiconductor stacked structure in common, the impurity element is introduced by selective diffusion in the absorption layer for each of the light-receiving elements, and the light-receiving elements are arranged one-dimensionally or two-dimensionally. According to this configuration, since the light-receiving elements are formed in individual impurity diffusion regions, element separation trenches need not be provided. Therefore, it is possible to form a light-receiving element array which is easily formed with high accuracy, and in which the dark current can be reduced.

A biological portion to be examined may be irradiated with light emitted from a supercontinuum light source (SC light source) or a light-emitting diode (LED), and light transmitted through or reflected from the biological portion may be received. In general, a halogen lamp is used as a light source. However, since a halogen lamp generates heat, the user may feel heat or an uncomfortable feeling by irradiation. In contrast, a SC light source or an LED does not generate heat, and thus such a light source is suitable for a light source for measurement related to a biological object. In the case of the SC light source or LED and the case of an ordinary halogen lamp, the biological component detection device of the present invention usually includes a control unit configured to operate on the basis of the results of the light reception performed by the light-receiving element or the light-receiving element array to calculate the concentration of a component contained in a biological object.

The biological component detection device may further include an imaging device including a two-dimensional array of the light-receiving element, in which a detection image of a component contained in the biological object which is a detection target may be formed with the imaging device. In this case, it is possible to obtain a distribution image of a predetermined component contained in the target object, the distribution image being easily understood sensuously.

The biological object may be irradiated with light in the wavelength region, and light reflected from the biological object or light transmitted through the biological object is received to detect at least one component selected from glucose, grape sugar, hemoglobin, cholesterol, albumin, active oxygen, fat, and collagen contained in the biological object. With this configuration, the concentrations of the sugar and cholesterol in the blood of humans can be easily known. As a result, people who are diabetic and people who are pre-diabetic, which account for several tens of percent of the population, can be routinely diagnosed with high accuracy, and thus the medical treatment or progression of the disease can be stopped. Furthermore, since the constituent concentration of blood vessels or the blood can be easily obtained, the biological component detection device is also useful for preventing adult diseases such as brain infarctions and cardiac infarctions. The user can readily obtain objective data regarding symptoms, such as those of metabolic syndrome, which can lead to the above diseases, and easily takes measures.

Furthermore, a lack of collagen, which is related to the generation of wrinkles at the tail of the eye, can be easily checked in the form of a distribution image by using the near-infrared imaging device. The device can be used for detecting various components, such as collagen, related to the beautiful skin.

The biological component detection device may further include a spectral separation unit configured to spectrally separate light; a plurality of the light-receiving elements or a light-receiving element array located in accordance with the spectrally separated wavelength; and a control unit configured to perform an operation on the basis of the results of light reception performed by the light-receiving elements or the light-receiving element array to calculate the concentration of the component of the biological object, the spectral separation unit being disposed on the irradiation side of the light of the detection portion or behind the detection portion when viewed from the irradiation side. With this configuration, multiwavelength simultaneous light reception or the like can be rapidly performed with high accuracy. The spectral separation unit is preferably formed of a diffraction grating or the like. The control unit may include a storage unit, an input unit from the outside, and the like, and a calibration curve of a target wavelength or the like may be input and stored in advance.

Advantages

According to the biological component detection device of the present invention, a biological component can be detected with high sensitivity by using an InP-based light-receiving element in which the dark current is reduced without providing a cooling mechanism and the sensitivity is extended to a wavelength of 1.8 μm or more.

REFERENCE NUMERALS

1 InP substrate, 2 buffer layer, 3 absorption layer having a multiple quantum well structure, 4 diffusion concentration distribution control layer, 5 InP window layer, 5a surface of window layer, 6 p-type region, 10 light-receiving element, 11 p-side electrode, 12 n-side electrode, 12b solder bump, 15 pn-junction, 35 anti-reflection film, 36 selective diffusion mask pattern, 27 wiring electrode, 43 SiON film, 50 light-receiving element array, 51 InP substrate, 61, 62, 63 light-receiving end, 66 selecting switch, 67 air pump, 68 pressure gauge, 69 air piping, 70 imaging device (detection device), 71 multiplexer (mounting substrate), 72 filter, 73 light source, 74 diffused plate, 75 actuator, 76 concave mirror, 77 casing, 77a biological object insertion trench, 81 irradiation optical fiber, 82 information-carrying optical fiber, 82a light-receiving end, 82b pressure-adjusting actuator, 83 probe, 84 optical fiber, 85 control unit, 85b microcomputer (operation unit, CPU), 85c display unit (output device), 87, 87a, 87b condenser lens, 91 diffraction grating (spectroscope), 95 table, 96 air bag, 100 biological component detection device, C cornea, E eye.

EMBODIMENT 1

Structure of Semiconductor Light-Receiving Element Array

Figure 1:
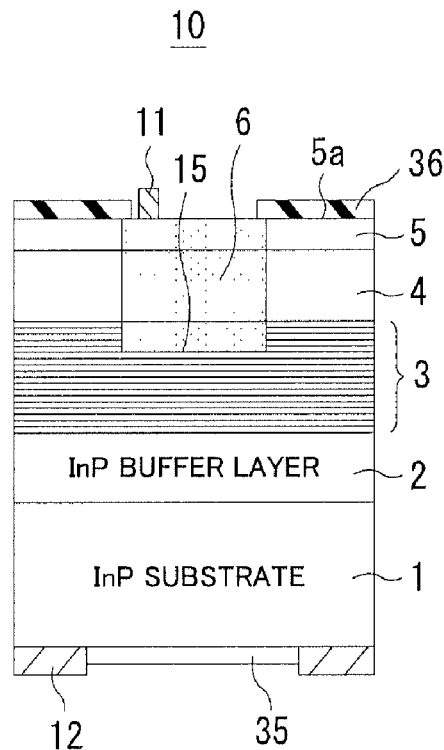
FIG. 1 is a cross-sectional view showing a light-receiving element according to Embodiment 1 of the present invention.

FIG. 1 is a cross-sectional view showing a light-receiving element 10 according to an embodiment of the present invention. Referring to FIG. 1, the light-receiving element 10 includes a group III-V semiconductor stacked structure (epitaxial wafer) disposed on an InP substrate 1 and having the following structure.
(InP substrate 1/InP buffer layer 2/absorption layer 3 having a multiple quantum well structure composed of InGaAs or GaInNAs and GaAsSb/InGaAs diffusion concentration distribution control layer 4/InP window layer 5)

A p-type region 6 extending from the InP window layer 5 to the absorption layer 3 having the multiple quantum well structure is formed by selectively diffusing Zn, which is a p-type impurity, from an opening of a selective diffusion mask pattern 36 composed of a SiN film. By performing diffusion using the selective diffusion mask pattern 36 composed of the SiN film, the p-type impurity can be introduced into the inside of the peripheral portion of the light-receiving element 10 by diffusion so that the diffusion in the peripheral portion is two-dimensionally limited.

A p-side electrode 11 made of AuZn and an n-side electrode 12 made of AuGeNi are provided on the p-type region 6 and the reverse face of the InP substrate 1, respectively, so as to form an ohmic contact. In this case, the InP substrate 1 is doped with an n-type impurity so as to have an electrical conductivity at a predetermined level. An anti-reflection film 35 made of SiON is also provided on the reverse face of the InP substrate 1 so that the light-receiving element 10 can be used when light is incident from the reverse face side of the InP substrate.

A pn-junction is formed in the absorption layer 3 having the multiple quantum well structure at a position corresponding to a boundary front of the p-type region 6. By applying a reverse bias voltage between the p-side electrode 11 and the n-side electrode 12, a depletion layer is more widely generated on the side in which the n-type impurity concentration is low (n-type impurity background). The background in the absorption layer 3 having the multiple quantum well structure has an n-type impurity concentration (carrier concentration) of about $5\times10^{15}/cm^3$ or less. The position 15 of the pn-junction is determined by an intersection between the background (n-type carrier concentration) of the absorption layer 3 having the multiple quantum well and a concentration profile of Zn, which is a p-type impurity. That is, the pn-junction 15 is located at the position shown in FIG. 2.

Figure 2:
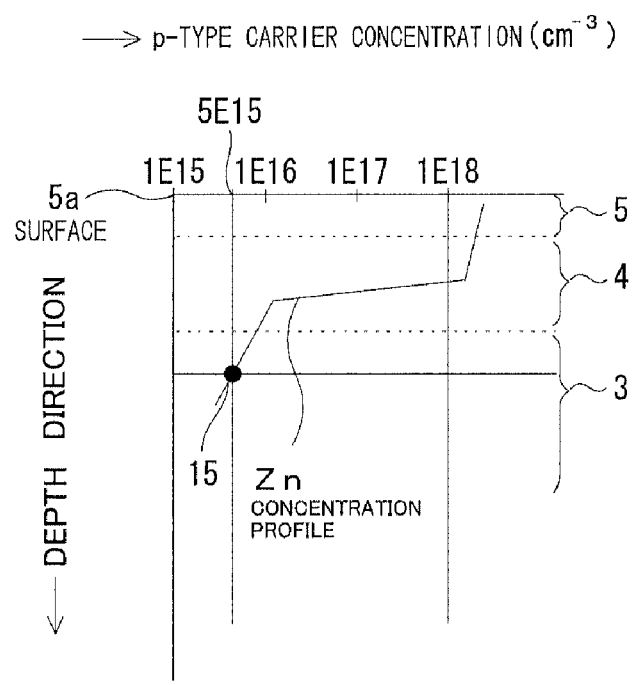
FIG. 2 is a drawing showing a Zn concentration distribution in the light-receiving element shown in FIG. 1.

In the diffusion concentration distribution control layer 4, the concentration of the p-type impurity that is selectively diffused from a surface 5a of the InP window layer 5 drastically decreases from a high-concentration region at the InP window layer side to the absorption layer side. Accordingly, in the absorption layer 3, a Zn concentration of $5\times10^{16}/cm^3$ or less can be easily realized as an impurity concentration. In FIG. 2, a lower Zn concentration of about $1\times10^{16}/cm^3$ or less is realized in the absorption layer 3.

Since the light-receiving element 10 targeted by the present invention aims to have sensitivity in the range from the near-infrared red region to the long-wavelength side thereof, the window layer is preferably composed of a material having a bandgap energy larger than the bandgap energy of the absorption layer 3. For this reason, InP, which is a material having a bandgap energy larger than that of the absorption layer and having a good lattice matching property, is usually used as the window layer. Alternatively, InAlAs, which has a bandgap energy substantially the same as that of InP, may also be used.

(Points of Light-Receiving Element Array of this Embodiment)

Features of this embodiment lie in that the following factors are included.

1. When a high concentration of an impurity is introduced into a multiple quantum well structure by selective diffusion, the multiple quantum well structure is broken. Therefore, it is necessary to suppress the amount of impurity introduced by the selective diffusion to be low. In general, it is necessary to control the concentration of the p-type impurity introduced by diffusion to be $5\times10^{16}/cm^3$ or less.

2. In order to stably achieve the above-mentioned low concentration of the p-type impurity with a good repeatability in the actual production, the diffusion concentration distribution control layer 4 composed of InGaAs is provided on the absorption layer 3. If, in the diffusion concentration distribution control layer 4, a thickness range at the absorption layer side has the above-mentioned low impurity concentration, the electrical conduction property in the low-impurity concentration range decreases or the electrical resistance in the low-impurity concentration range increases. When the electrical conduction property of the low-impurity concentration range in the diffusion concentration distribution control layer 4 decreases, the responsiveness decreases, and, for example, good moving images cannot be obtained. However, in the case where the diffusion concentration distribution control layer is composed of a material having a bandgap energy smaller than the bandgap energy corresponding to that of InP, specifically, a group III-V semiconductor material having a bandgap energy less than 1.34 eV, even if the impurity concentration is low, the electrical conduction property does not very significantly decrease. An example of the group III-V semiconductor material that satisfies the above requirement of the diffusion concentration distribution control layer is InGaAs.

The reason why the impurity concentration of the absorption layer is controlled to be $5\times10^{16}/cm^3$ or less will be described in more detail. If the Zn concentration in the absorption layer 3 exceeds $1\times10^{17}$ cm$^{-3}$ because, for example, the depth of the selective diffusion of the p-type impurity (Zn) is increased, in the resulting high-concentration portion having a Zn concentration of more than $1\times10^{17}$ cm$^{-3}$, atoms of InGaAs and GaAsSb constituting the quantum well layers are disordered to each other, whereby a superlattice structure is broken. The crystal quality of the broken portion degrades, thereby degrading characteristics of the element, for example, increasing the dark current. Here, the Zn concentration is usually measured by secondary ion mass spectroscopy (SIMS). However, it is difficult to analyze a concentration on the order of $10^{17}$ cm$^{-3}$ or $10^{16}$ cm$^{-3}$, and a relatively large measurement error is generated. The above detailed description concerns a discussion about the values of the Zn concentration with a double or half accuracy, and this is resulted from this roughness of the measurement accuracy. Accordingly, for example, discussing a difference between $5\times10^{16}/cm^3$ and $6\times10^{16}/cm^3$ is difficult because of the low measurement accuracy, and is not so significant.

By using a material having a narrow bandgap energy as the diffusion concentration distribution control layer, an increase in the electrical resistance can be suppressed even at a low impurity concentration. It is believed that the response time to the application of a reverse bias voltage or the like is determined by the CR time constant determined by the capacitance and the electrical resistance. Accordingly, the response time can be shortened by suppressing the increase in the electrical resistance R as described above.

3. In this embodiment, the multiple quantum well structure has a type-II structure. In a type-I quantum well structure, in the case of a light-receiving element having a structure in which a semiconductor layer having a small bandgap energy is sandwiched between semiconductor layers having a large bandgap energy so as to have sensitivity in the near-infrared region, the upper limit of the wavelength (cutoff wavelength) of the sensitivity is determined by the bandgap of the semiconductor layer having the small bandgap energy. That is, the transition of electrons or holes caused by light is performed in the semiconductor layer having the small bandgap energy (direct transition). In this case, a material that extends the cutoff wavelength to a longer-wavelength range is very limited among group III-V compound semiconductors. In contrast, in the type-II quantum well structure, when two different types of semiconductor layers having the same Fermi energy are alternately stacked, an energy difference between the conduction band of a first semiconductor and the valence band of a second semiconductor determines the upper limit of the wavelength (cutoff wavelength) of the sensitivity. That is, the transition of electrons or holes caused by light is performed between the valence band of the second semiconductor and the conduction band of the first semiconductor (indirect transition). Therefore, by controlling the energy of the valence band of the second semiconductor to be higher than the energy of the valence band of the first semiconductor, and controlling the energy of the conduction band of the first semiconductor to be lower than the energy of the conduction band of the second semiconductor, the sensitivity can be easily extended to the long-wavelength side, as compared with the case of the direct transition performed in a single semiconductor.

4. As described above, the p-type impurity is introduced into the inside of the peripheral portion of the light-receiving element by diffusion so that the diffusion in the peripheral portion is two-dimensionally limited by performing selective diffusion using the selective diffusion mask pattern. Accordingly, the pn-junction descried above is not exposed on the end faces of the light-receiving element. As a result, leakage of a photocurrent is suppressed.

Figure 3:
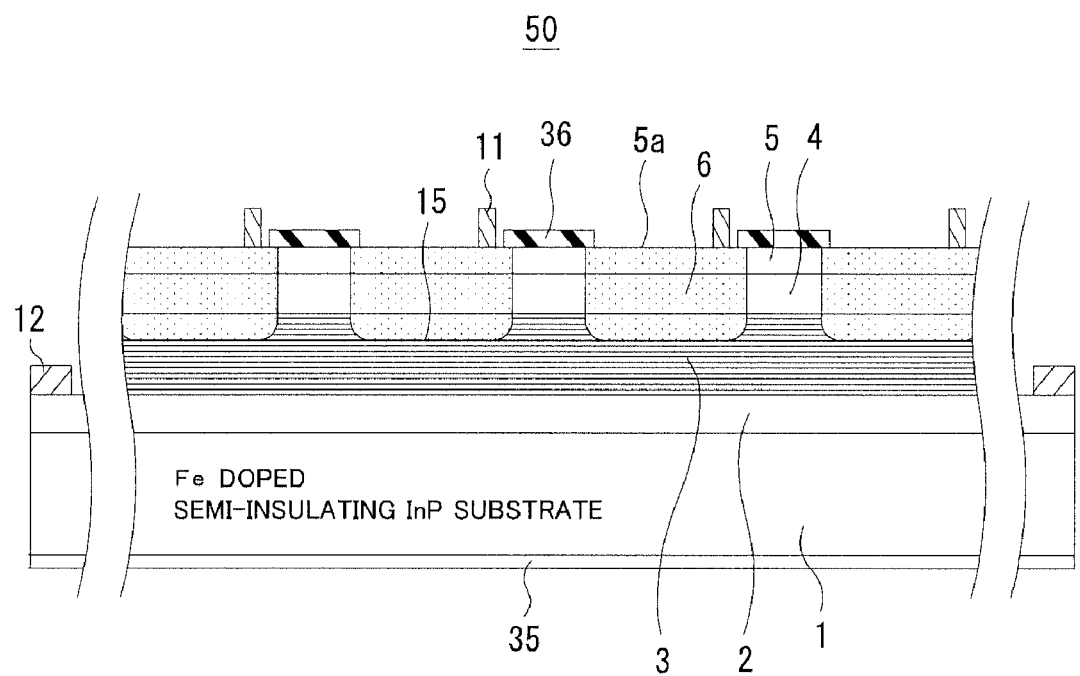
FIG. 3 is a cross-sectional view showing a light-receiving element array according to Embodiment 1 of the present invention.

FIG. 3 is a cross-sectional view showing a light-receiving element array 50 in which a plurality of the light-receiving elements 10 described above are arranged on an epitaxial wafer including a common InP substrate. A feature of this light-receiving element array 50 lies in that the plurality of light-receiving elements 10 are arranged without element separation trenches. As described in item 4 above, a p-type region 6 is limited inside each of the light-receiving elements, and is reliably separated from adjacent light-receiving elements. An absorption layer 3 is formed so as to have a multiple quantum well structure, a diffusion concentration distribution control layer 4 is disposed on the absorption layer 3, and the p-type impurity concentration in the absorption layer 3 is controlled to be $5 \times 10^{16}/cm^3$ or less. These points etc. are the same as those of the light-receiving element 10 shown in FIG. 1.

Next, a method for producing the light-receiving element 10 shown in FIG. 1 will be described. An InP buffer layer 2 or InGaAs buffer layer 2 having a thickness of 2 μm is deposited on an n-type InP substrate 1. Subsequently, an absorption layer 3 having a multiple quantum well structure composed of (InGaAs/GaAsSb) or (GaInNAs/GaAsSb) is formed. The composition of InGaAs is determined to be $In_{0.53}Ga_{0.47}As$ and the composition of GaAsSb is determined to be $GaAs_{0.52}Sb_{0.48}$ so that these materials are lattice-matched to InP. Thus, a degree of lattice matching (|Δa/a|: where a represents a lattice constant and Δa represents a difference in the lattice constant between the two) is 0.002 or less. The thickness of the InGaAs layer (or the GaInNAs layer) forming a unit quantum well structure is 5 nm, and the number of pairs (the number of repetitions of the unit quantum well) is 300. Subsequently, as a diffusion concentration distribution control layer 4, which functions in the introduction of Zn by diffusion, an InGaAs layer having a thickness of 1 μm is epitaxially grown on the absorption layer 3. Lastly, an InP window layer 5 having a thickness of 1 μm is then epitaxially grown. Both the absorption layer 3 and the diffusion concentration distribution control layer 4 are preferably epitaxially grown by a molecular beam epitaxy (MBE) method. The InP window layer 5 may be epitaxially grown by the MBE method. Alternatively, the InP substrate 1 may be taken out from an MBE apparatus after the growth of the diffusion concentration control layer 4, and the InP window layer 5 may be epitaxially grown by a metal organic vapor phase epitaxy (MOVPE) method.

The InP buffer layer 2 or the InGaAs buffer layer 2 may be non-doped or may be doped with an n-type dopant such as silicon (Si) in a concentration of about $1 \times 10^{17}/cm^3$. The absorption layer 3 having the multiple quantum well structure composed of GaInNAs/GaAsSb, the diffusion concentration distribution control layer 4 composed of InGaAs, and the InP window layer 5 are preferably non-doped. However, these layers may be doped with a trace amount (for example, about $2 \times 10^{15}/cm^3$) of an n-type dopant such as Si. Furthermore, a high-concentration n-side electrode formation layer for forming an n-side electrode, the n-side electrode formation layer being doped with an n-type dopant of about 1E18 $cm^{-3}$, may be interposed between the InP substrate 1 and the buffer layer 2. The InP substrate 1 may be an Fe-doped semi-insulating InP substrate. In this case, the n-side electrode formation layer doped with the n-type dopant of about $1 \times 10^{18}/cm^3$ is interposed between the semi-insulating InP substrate 1 and the buffer layer 2.

An optical device is produced using the stacked structure (epitaxial wafer) including the InP substrate 1 described above. Selective diffusion of Zn is performed from an opening of a SiN mask pattern 36 formed on a surface 5a of the InP window layer 5. Thus, a p-type region 6 is formed so as to extend in the absorption layer 3 having the InGaAs/GaAsSb (or GaInNAs/GaAsSb) multiple quantum well structure. A front end portion of the p-type region 6 forms a pn-junction 15. In this case, a high-concentration region having a Zn concentration of about $1 \times 10^{18}/cm^3$ or more is limited in the InGaAs diffusion concentration distribution control layer 4. That is, the above high-concentration impurity distribution continues from the surface 5a of the InP window layer 5 to the inside of the InGaAs diffusion concentration distribution control layer 4 in the depth direction, and decreases to $5 \times 10^{16}/cm^3$ or less at a deeper position in the diffusion concentration distribution control layer 4. The Zn concentration distribution near the pn-junction 15 shows a graded junction.

As for a one-dimensional or two-dimensional arrangement of the light-receiving elements 10, that is, the light-receiving element array shown in FIG. 3, adjacent light-receiving elements are separated from each other by performing selective diffusion of Zn (diffusion that is two-dimensionally limited so that a diffused portion is disposed inside a peripheral portion of each light-receiving element) without performing mesa etching for element separation. Specifically, the Zn selective diffusion region 6 constitutes a main portion of one light-receiving element 10 and forms one pixel, and regions where Zn does not diffuse separate respective pixels from each other. Therefore, the light-receiving element array does not suffer from, for example, crystal damage caused by mesa etching, and thus a dark current can be suppressed.

Patent Document 10 describes a concern that, in the case where a pn-junction is formed by selective diffusion of an impurity, the distance between elements cannot be decreased to a certain dimension or less because the impurity diffuses not only in the depth direction but also in the lateral direction (the direction orthogonal to the depth direction). However, according to an experimental result of selective diffusion of Zn, it was confirmed that, in the structure in which the InP window layer 5 is disposed on the top surface and the InGaAs diffusion concentration distribution control layer 4 is disposed under the InP window layer 5, the area of the diffusion in the lateral direction is substantially the same as or smaller than the area of the diffusion in the depth direction. That is, in selective diffusion of Zn, although Zn diffuses in the lateral direction so that the diameter of a diffusion region is larger than the diameter of an opening of a mask pattern, the degree of diffusion is small and the region is only slightly expanded from the opening of the mask pattern, as schematically shown in, for example, FIGS. 1 and 3.

Figure 4:
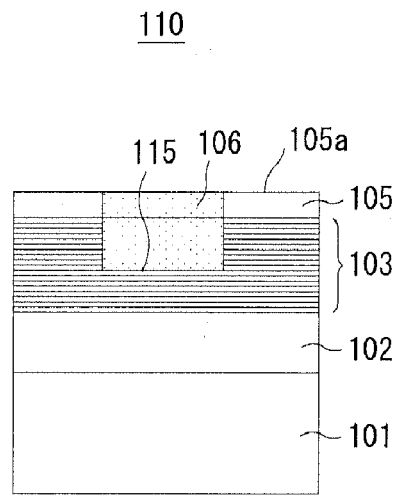
FIG. 4 is a cross-sectional view of a light-receiving element of Reference Example 1 that is different from the present invention.

FIG. 4 is a cross-sectional view of a light-receiving element 110 of Reference Example 1 that is different from the present invention. The light-receiving element 110 of Reference Example 1 has the following stacked structure.
(InP substrate 101/InP or InGaAs buffer layer 102/absorption layer 103 having (GaInNAs/GaAsSb) multiple quantum well structure/InP window layer 105)

A p-type region 106 is formed by performing selective diffusion using a selective diffusion mask pattern so as to extend from a surface 105a of the InP window layer 105 into the absorption layer 103. A pn-junction 115 is formed on the leading end of the p-type region 106. This stacked structure differs from the stacked structure of the embodiment of the present invention in that the diffusion concentration distribution control layer is not provided. That is, the absorption layer 103 having the multiple quantum well structure is disposed directly under the InP window layer 105.

Figure 5:
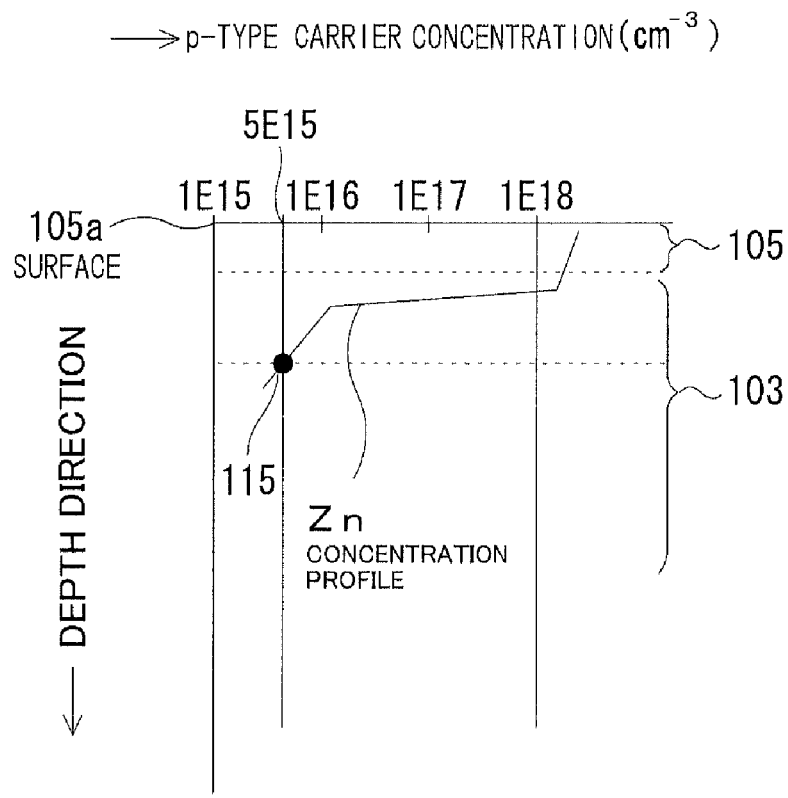
FIG. 5 is a drawing showing a Zn concentration distribution in the light-receiving element shown in FIG. 4.

When the diffusion concentration distribution control layer is not provided, as shown in FIG. 5, for example, as for the Zn concentration distribution, a high-concentration impurity region extends to the absorption layer 103 having the multiple quantum well structure. Specifically, in the multiple quantum well structure, a high-concentration impurity region of $1 \times 10^{18}/cm^3$, which exceeds $5 \times 10^{16}/cm^3$, is formed. When a high-concentration impurity is introduced in the multiple quantum well structure, the structure is broken, and the dark current significantly increases. In order to prevent such a high-concentration impurity region from being formed in the multiple quantum well structure, the diffusion concentration distribution control layer is formed, and selective diffusion is then performed.

However, there is a possibility for realizing the following ideas regarding the selective diffusion of Zn.
(1) The time required for introduction by diffusion is limited to be short so that a high-concentration region does not reach the multiple quantum well structure 103.
(2) The thickness of the InP window layer 105 is increased so that the InP window layer 105 has the function of the diffusion concentration distribution control layer.

Figure 6:
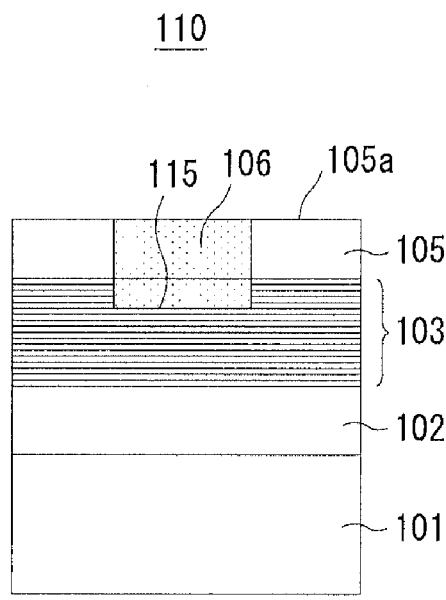
FIG. 6 is a cross-sectional view of a light-receiving element of Reference Example 2 that is different from the present invention.
Figure 7:
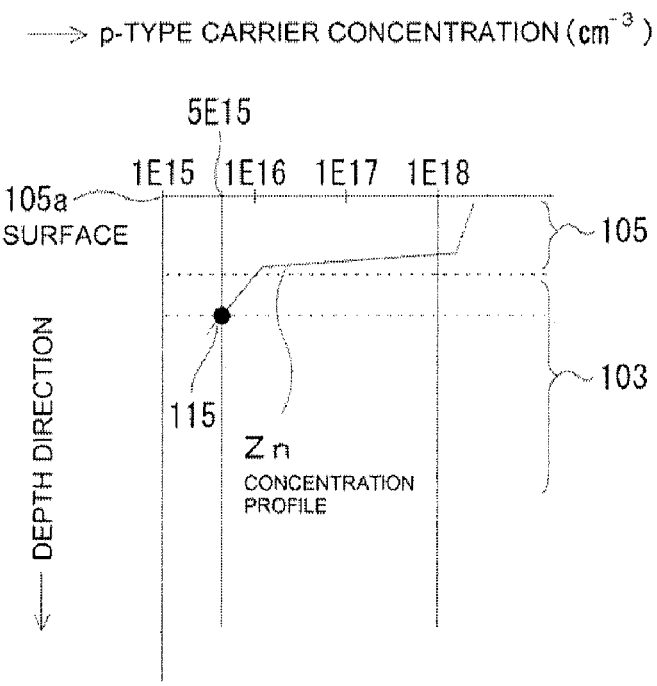
FIG. 7 is a drawing showing a Zn concentration distribution in the light-receiving element shown in FIG. 6.

FIG. 6 is a cross-sectional view showing a light-receiving element 110 of Reference Example 2 for examining the cases of (1) and (2) described above. The light-receiving element 110 of Reference Example 2 has a stacked structure substantially the same as that of the light-receiving element of Reference Example 1, but the thickness of an InP window layer 105 is larger than that of Reference Example 1. The light-receiving element 110 of Reference Example 2 corresponds to the case of (2) above, but can also be used for examining the case of (1) above. In the stacked structure shown in FIG. 6, selective diffusion is performed so that a high-concentration region of Zn is not formed in the multiple quantum well structure 103. Consequently, a Zn concentration distribution shown in FIG. 7 is obtained. In the case of the Zn concentration distribution shown in FIG. 7, in the InP window layer 105, the Zn concentration drastically decreases from a high concentration to a low concentration, and a low-concentration impurity region with a concentration of about $1 \times 10^{16}/cm^3$ is formed in the InP window layer 105 at the absorption layer side.

When the low-concentration impurity region with a concentration of about $1 \times 10^{16}/cm^3$ is formed in the InP window layer 105, the electrical resistance in the region increases, thereby decreasing the response time, as repeatedly described above. Accordingly, the function of the diffusion concentration distribution control layer cannot be provided to a material having a bandgap energy that is large enough to form the window layer, specifically, to the InP window layer 105, which is a typical example composed of such a material. This applies to both the cases of (1) and (2) above. Accordingly, a material having a bandgap energy corresponding to that of InP or less, specifically, a material that satisfies a bandgap energy of less than 1.34 eV is preferably used as the diffusion concentration control layer. That is, it is necessary to use a material, such as InGaAs, in which a decrease in the electrical conductivity is relatively small and an increase in the electrical resistance is relatively small even in a low-concentration impurity region.

EMBODIMENT 2

Figure 8:
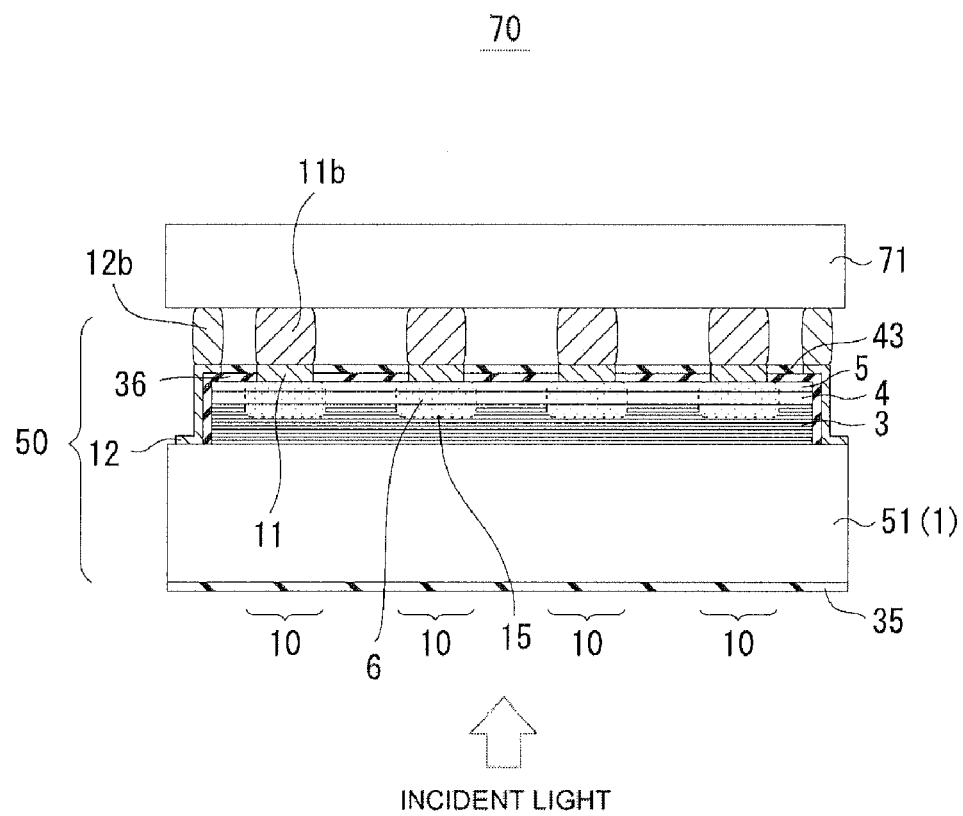
FIG. 8 is a view showing the outline of an imaging device according to Embodiment 2 of the present invention.
Figure 9:
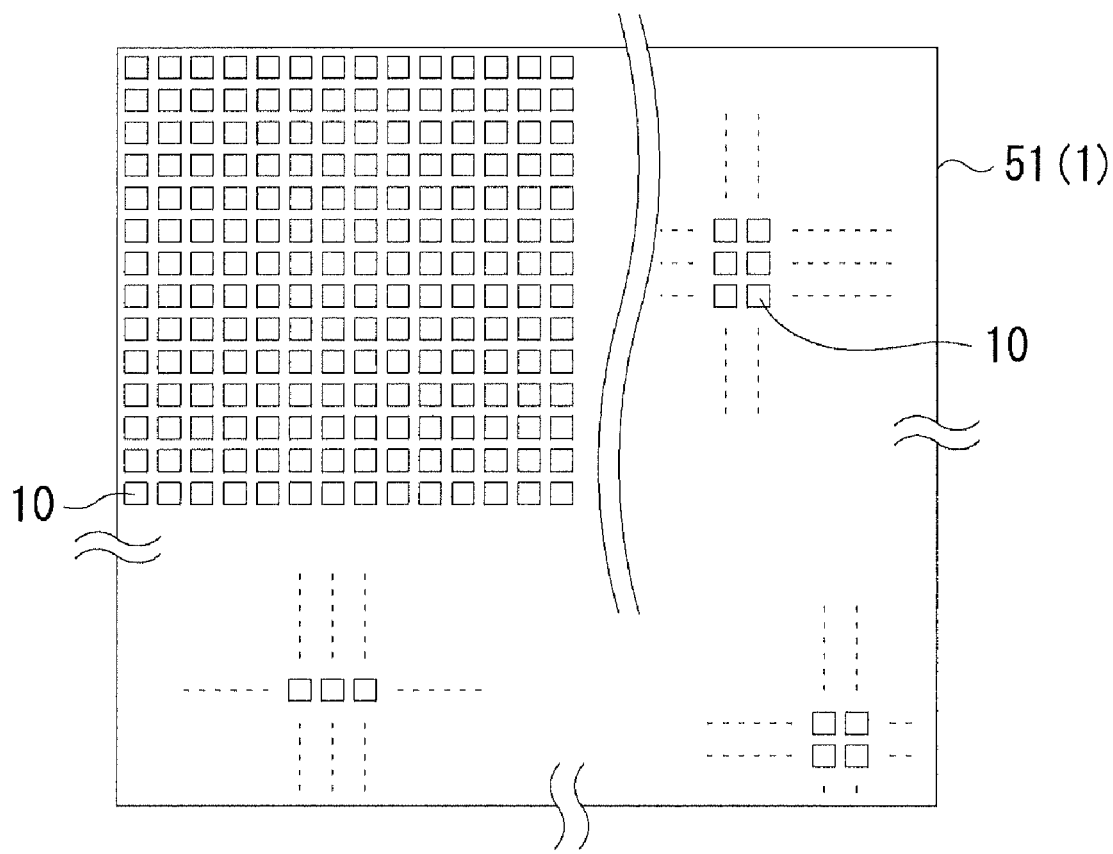
FIG. 9 is a view showing a light-receiving element array of the imaging device shown in FIG. 8.
Figure 10:
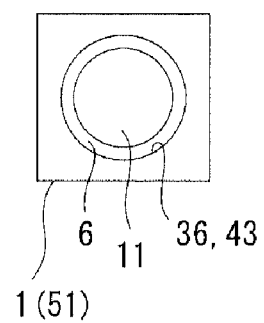
FIG. 10 is a view showing one light-receiving element in the light-receiving element array shown in FIG. 9.

Structure of Imaging Device (Device for Forming Distribution Image of Component) in Biological Component Detection Device FIG. 8 is a view showing the outline of an imaging device (light-receiving element array) included in a biological component detection device according to Embodiment 2 of the present invention. Optical members such as a lens are omitted. FIG. 9 is a view illustrating a light-receiving element array 50 of the imaging device or a detection device (image sensor) 70. FIG. 10 is a view showing a single light-receiving element in the light-receiving element array 50 shown in FIG. 9. In FIG. 8, in this imaging device 70, light-receiving elements 10 provided on a common InP substrate 51 are epi-side-down mounted so that the epitaxial layer side of the light-receiving elements 10 face a multiplexer 71 having a function of a mounting substrate. A p-side electrode 11 that is electrically connected to a p-type region 6 of an epitaxial layer of each of the light-receiving elements 10 and an n-side electrode 12 provided on the common n-type InP substrate 51 (1) are connected to the multiplexer 71 and send electrical signals to the multiplexer 71. The multiplexer 71 receives the electrical signals from each of the light-receiving elements and performs a process for forming a whole image of an object. The n-side electrode 12 and the p-side electrode 11 are electrically connected to the multiplexer 71 via solder bumps 12b and 11b, respectively. Incident light enters through an anti-reflection (AR) film 35 provided on the reverse face of the InP substrate 51 and is received in a pn-junction 15 which is a boundary face between the p-type region 6 and an absorption layer 3. The p-type region 6 is introduced from an opening of a Zn diffusion mask 36 that is composed of SiN and that also functions as a protective film. The Zn diffusion mask pattern 36 is left as it is together with a SiON film pattern 43 functioning as a protective film and provided on the mask pattern 36. The structures of the light-receiving element array and each of the light-receiving elements will now be described in detail with reference to FIGS. 9 and 10, respectively.

In FIG. 9, light-receiving elements 10 of a light-receiving element array 50 are provided on a common InP substrate 51 (1). Current signals generated by receiving light in a short wave infrared (SWIR) band in each of the light-receiving elements are sent to a multiplexer 71, which also functions as a mounting substrate, and undergo a process for forming an image, as described above. The number of pixels is changed by changing the size and the pitch of each of the light-receiving elements and the size of the array. The light-receiving element array 50 shown in FIG. 9 has 90,000 pixels. The light-receiving element 10 shown in FIG. 10 includes a plurality of epitaxial films formed on an InP substrate 1. A diffusion mask 36 for introducing a p-type impurity, the diffusion mask 36 having been used in forming a p-type region 6, is left in the light-receiving element 10. A p-portion electrode 11 is connected to the p-type region 6, and is connected to, for example, wiring of a mounting substrate such as the multiplexer 71 via a solder bump or the like.

Figure 11:
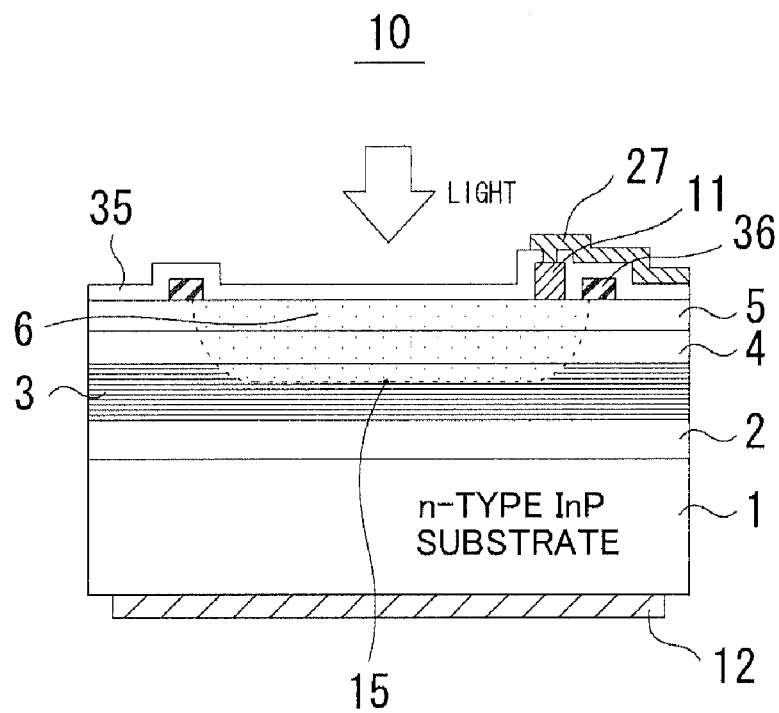
FIG. 11 is a cross-sectional view of a light-receiving element of epi-side up mounting.

FIG. 11 is a cross-sectional view illustrating a light-receiving element that is epi-side-up mounted, which is different from the epi-side down light-receiving element shown in FIG. 8. In the present invention, the light-receiving element in the imaging device may be epi-side-down mounted or epi-side-up mounted. In this light-receiving element 10, from the bottom, an n-type InP buffer layer 2, an absorption layer 3, a diffusion concentration distribution control layer 4, an InP window layer 5, a diffusion mask 36, and an AR film 35 are sequentially disposed on an n-type InP substrate 1. A p-type region 6 is formed so as to extend from the InP window layer 5 to a pn-junction 15 in the absorption layer 3 through the diffusion concentration distribution control layer 4. In addition, an n-side electrode 12 is disposed on the reverse face of the n-type InP substrate. A p-side electrode 11 is disposed on the surface of the InP window layer 5 of the p-type region 6 and is electrically connected to a wiring electrode 27. In this embodiment, the absorption layer 3 receives light having a wavelength in the range of 1.0 to 3.0 μm. Specifically, the absorption layer 3 is formed of the above-described type-II multiple quantum well structure.

Figure 12:
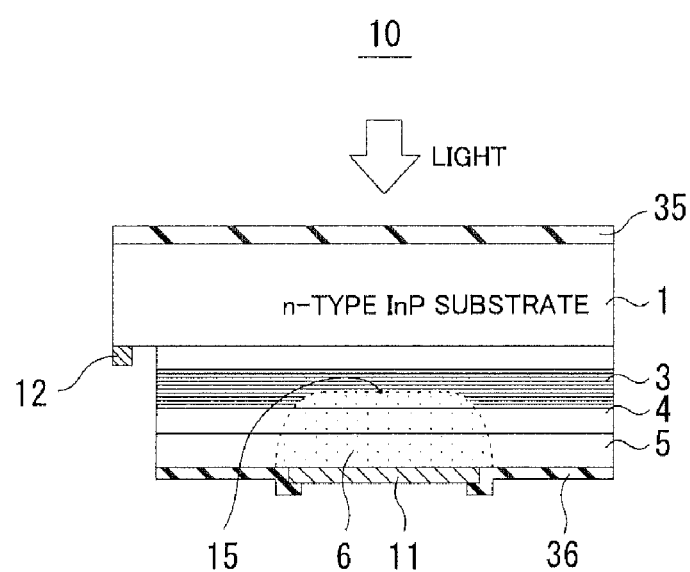
FIG. 12 is a cross-sectional view of a light-receiving element of epi-side down (flip-chip) mounting.

The light-receiving element shown in FIG. 11 is epi-side-up mounted as described above. Light is incident from the epitaxial layer side, i.e., the InP window layer 5 side. The light-receiving element of this embodiment may be epi-side-up mounted or epi-side-down mounted as describe above. As shown in FIG. 12, the light-receiving element 10 may be epi-side-down mounted, and light may be incident from the reverse face side of the InP substrate 1. In the case of the epi-side-down mounted light-receiving element 10 shown in FIG. 12, an AR film 35 is provided on the reverse face of the InP substrate 1. A diffusion concentration control layer 4, an InP window layer 5, a p-side electrode 11, and a SiN diffusion mask 36 that also functions as a protective film are provided as in the case of the epi-side-up mounting. In the epi-side-down mounting shown in FIG. 12, InP constituting the InP substrate and other components is transparent to light in the SWIR band. Accordingly, the light in the SWIR band reaches a pn-junction 15 of an absorption layer 3 without being absorbed. Also in the structure shown in FIG. 12, the absorption layer is formed of the above-described type-II multiple quantum well structure. This also applies to embodiments of the present invention described below unless otherwise stated.

As shown in FIG. 11, the p-side electrode 11 and the n-side electrode 12 may be disposed at positions facing each other with the InP substrate 1 therebetween. Alternatively, as shown in FIG. 12, the p-side electrode 11 and the n-side electrode 12 may be disposed at positions on the same side of the InP substrate 1. In the structure shown in FIG. 12, each of the light-receiving elements 10 of the light-receiving element array 50 shown in FIG. 9 is electrically connected to an integrated circuit by flip-chip mounting. In the light-receiving elements having the structures shown in FIGS. 11 and 12, light incident on the pn-junction 15 is absorbed to generate current signals. Each of the current signals is converted to an image of one pixel through the integrated circuit, as described above.

The InP substrate 1 is preferably an off-angle substrate which is tilted at 5 to 20 degrees from (100) in the [111] direction or the [11-1] direction. More preferably, the substrate is tilted at 10 to 15 degrees from (100) in the [111] direction or the [11-1] direction. By using such a substrate having a large off-angle, it is possible to obtain an n-type InP buffer layer 2, an absorption layer 3 having a type-II quantum well structure, an InGaAs diffusion concentration distribution control layer 4, and an InP window layer 5, all of which have a low defect density and good crystal quality. As a result, a light-receiving element array or detection device in which a dark current is suppressed and the number of dark spots is small can be obtained. Accordingly, it is possible to obtain an absorption layer that is capable of markedly improving the performance of a device that receives faint cosmic light in the SWIR band to acquire an image. That is, the operation of the light-receiving element formed using the above-mentioned off-angle substrate is particularly useful for improving the quality of an imaging device that receives cosmic light to acquire an image.

The above-mentioned large off-angle of an InP substrate has not been proposed to date, and the above advantage due to the use of such an InP substrate has been confirmed for the first time by the inventors of the present invention. The large off-angle of an InP substrate is an important factor in the case where an epitaxial film having a good crystal quality is grown on the InP substrate. For example, in the case where an absorption layer 3 having the above-described quantum well structure, the absorption layer 3 being supposed to be able to emit and receive light in a very long-wavelength range, contains a nitrogen (N)-containing compound semiconductor, for example, GaInNAs, in reality, the absorption layer 3 cannot be formed as a satisfactory epitaxial layer that can withstand practical use, unless an InP substrate having such a large off-angle is used. That is, a nitrogen-containing compound semiconductor, for example, GaInNAs cannot be formed into an absorption layer in which a dark current is suppressed and the number of dark spots is reduced, unless such an InP substrate having the above large off-angle is used. Consequently, it is impossible to obtain a sharp image using faint cosmic light in the SWIR band. Not only GaInNAs cited as an example above, but also GaInNAsP and GaInNAsSb are common in that the above-mentioned range of a large off-angle of the InP substrate is necessary in order to obtain a good crystal quality.

Each of the light-receiving elements 10 shown in FIGS. 11 and 12 includes the InGaAs diffusion concentration control layer 4 and the InP window layer 5 that are disposed so as to cover the absorption layer 3. Since a lattice constant of the absorption layer 3 is the same as that of the InP substrate 1, the InGaAs diffusion concentration control layer 4 and InP window layer 5, which can reliably reduce the dark current, can be formed on the absorption layer 3. Consequently, the dark current can be suppressed to improve reliability of the element.

EMBODIMENT 3

Figure 13:
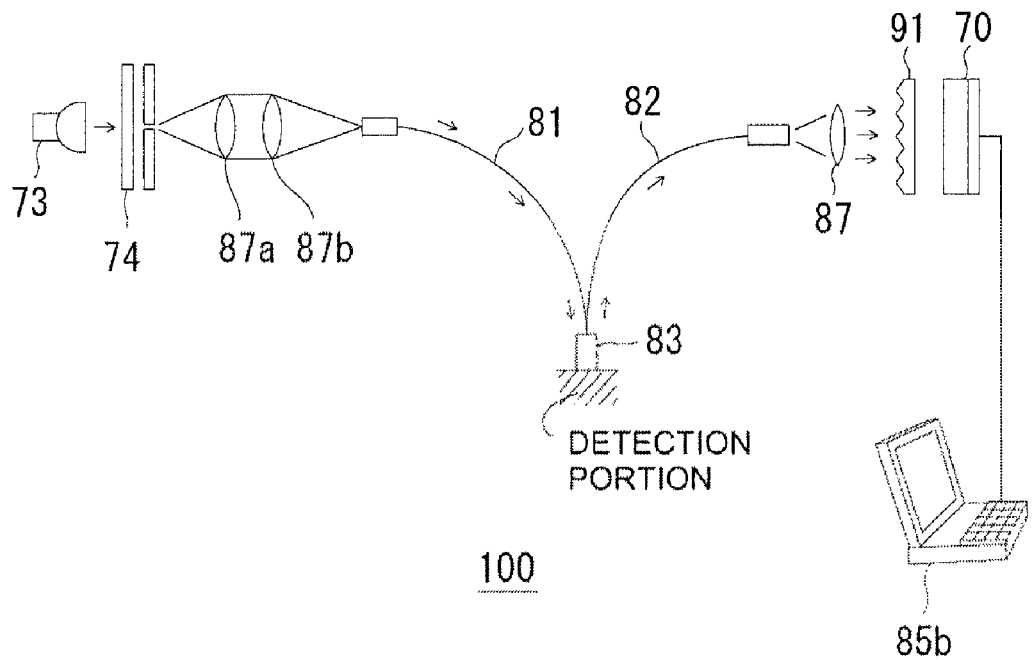
FIG. 13 is a view showing a biological component detection device (1) according to Embodiment 3 of the present invention.
Figure 14:
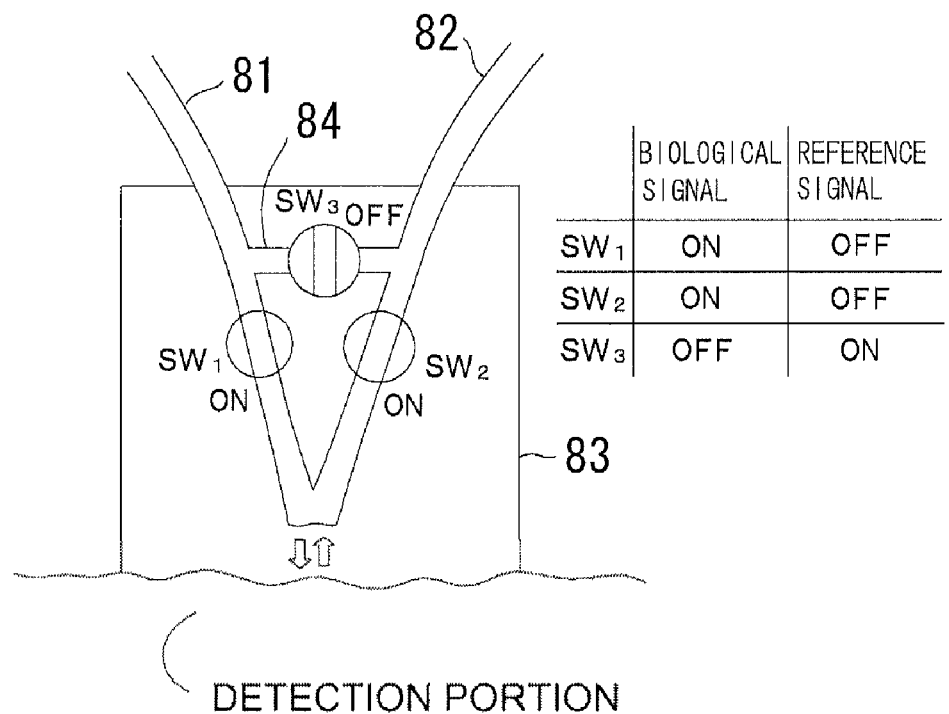
FIG. 14 is an enlarged view of a probe of the biological component detection device shown in FIG. 13.

Biological Component Detection Device (1)—Blood Sugar Level: Measurement by using Reflected Light FIG. 13 is a view showing a biological component detection device 100 according to Embodiment 3 of the present invention. FIG. 14 is a view showing a probe in the biological component detection device 100 shown in FIG. 13. It is important for diabetics to know their blood sugar level. When the blood sugar level rises, the blood sugar level is decreased by administrating insulin. Therefore, the patients routinely measure their blood sugar level. If the blood sugar level can be noninvasively measured with high accuracy without collecting the blood, this is preferable for the patients.

A method of noninvasive measurement of the blood sugar level is based on the fact that the glucose concentration in the skin tissue has a high positive correlation with the glucose concentration in the blood, and the glucose concentration in the skin tissue is used as the blood sugar level. The glucose concentration in the skin tissue is very low, i.e., in the range of several tens of to several hundred mg/dl. Accordingly, it is necessary to irradiate the skin with near-infrared light and to detect light transmitted through or diffusely reflected from the skin tissue with high accuracy.

In order to measure the concentration of a very small amount of glucose with high accuracy, it is effective to use two or more absorption bands in the absorption bands of glucose in the near-infrared region. Glucose has a large number of absorption bands in the wavelength range of 1 to 3 μm. However, as long as an existing InGaAs array is used, only near-infrared light having a wavelength of 1.7 μm or less is measured with high accuracy, and light in absorption bands in the longer-wavelength range cannot be measured with high accuracy. As shown in FIG. 13, by using the detection device 70 shown in FIG. 8, light can be extensively received up to a wavelength of 3.0 μm. Furthermore, by aligning the position of a diffraction grating 91 with the position of a light-receiving element array 50, an absorption spectrum of glucose can be measured by performing irradiation and light reception once (one time). Accordingly, the glucose concentration can be easily measured by using an absorption band of a wavelength of 1.8 μm or more. Thus, a very small amount of glucose in the skin can be easily measured with high accuracy.

There are the following factors for increasing the measurement accuracy of the glucose concentration. Stability of the spectrum measurement can be improved by suppressing a variation in the absorbance or the baseline as much as possible. Examples of the factors of a device, the factors giving a variation to a spectrum to be measured, include a variation in the positional relationship between components such as a light source and a light-receiving element unit, and a variation in the environmental temperature with time. To compensate for these variations, in general, a reference signal that is reflected from a reference plate such as a ceramic plate is measured separately from a biological signal, and the reference signal is used as standard light. Therefore, in order to stably perform the spectrum measurement, it is important that the reference signal can be stably measured.

When FIG. 13 is taken as an example, near-infrared light in the measurement of a detection portion has the following path:

light source 73→diffused plate 74→irradiation optical fiber 81→sensing unit (probe) 83→detection portion→sensing unit (probe) 83→information-carrying optical fiber 82→diffraction grating (spectroscope) 91→detection device 70→microcomputer 85b for calculating concentration When the near-infrared light has the above path, a probe connected to an irradiation optical fiber and an information-carrying optical fiber is applied to a detection portion (skin). On the other hand, in the measurement of the reference signal, only the detection portion is replaced with the reference plate. An operation of detaching the probe from the skin and bringing the probe into contact with the reference plate is performed. The microcomputer for calculating a concentration calculates the glucose concentration on the basis of the reference signal and the biological signal.

In the measurement of the reference signal by the method described above, repeatability of the positions of the probe and the reference plate varies, and a measurement time difference between the reference signal and the biological signal arises. Repetition of the above operations in each measurement makes stable measurement of the reference signal difficult. For this reason, hitherto, it has not been possible to sufficiently compensate for the instability of the spectrum measurement due to the variation in the reference signal, and it has been difficult to analyze the glucose concentration with high accuracy. The probe 83 shown in FIG. 14 eliminates this instability of the measurement of the reference signal. Without performing the measurement of the reference plate, directly, an optical fiber 84 connecting the irradiation optical fiber 81 to the information-carrying optical fiber 82 is arranged, and switches SW1, SW2, and SW3 are provided in the optical fibers 81, 82, and 84, respectively. With this structure, the variation in the repeatability of the positions of the probe and the reference plate is eliminated, and the measurement time difference between the reference signal and the biological signal is reduced. The switches SW1, SW2, and SW3 may be manual switches or automatic switches that are automatically turned on and off in response to the instruction from the microcomputer 85b.

EMBODIMENT 4

Figure 15:
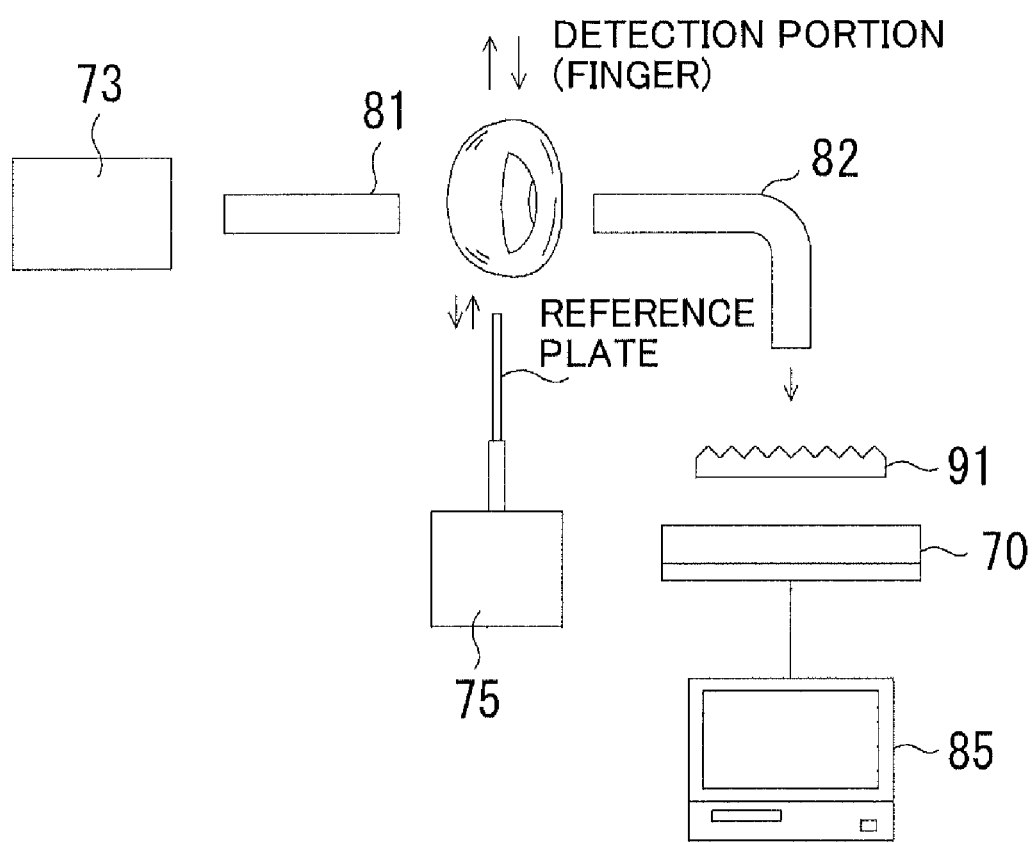
FIG. 15 is a view showing a biological component detection device (2) according to Embodiment 4 of the present invention.

Biological Component Detection Device (2)—Blood Sugar Level: Measurement by using Transmitted Light FIG. 15 is a view showing a biological component detection device 100 according to Embodiment 4 of the present invention. In FIG. 15, this embodiment is common to Embodiment 3 in that the above-described detection device 70 is used in a light-receiving unit and a concentration measurement is performed by using an absorption band of glucose, the absorption band being located in the long-wavelength range of the near-infrared region. This embodiment differs from Embodiment 3 in that the glucose concentration is determined by measuring near-infrared light transmitted through a biological object. In the example shown in FIG. 15, light transmitted through a person's finger is received, and many types of information about biological tissue such as the skin, the muscle, and the blood can be obtained.

A reference signal is measured on the basis of light transmitted through a reference plate that is retracted when a biological object (finger) is placed in position and that is placed in position when the biological object is retracted. The thickness of the reference plate is preferably small so that a sufficient amount of transmitted light is obtained, though the thickness depends on the material of the reference plate. The reference plate is moved by an actuator 75 so that variations in position and orientation (angle) are not generated.

Instead of using the reference plate described above, as shown in FIG. 14, an optical fiber 84 connecting, in a bypass manner, an irradiation optical fiber 81 to an information-carrying optical fiber 82 may be arranged, and switches may be provided in the optical fibers 81, 82, and 84, respectively.

EMBODIMENT 5

Figure 16:
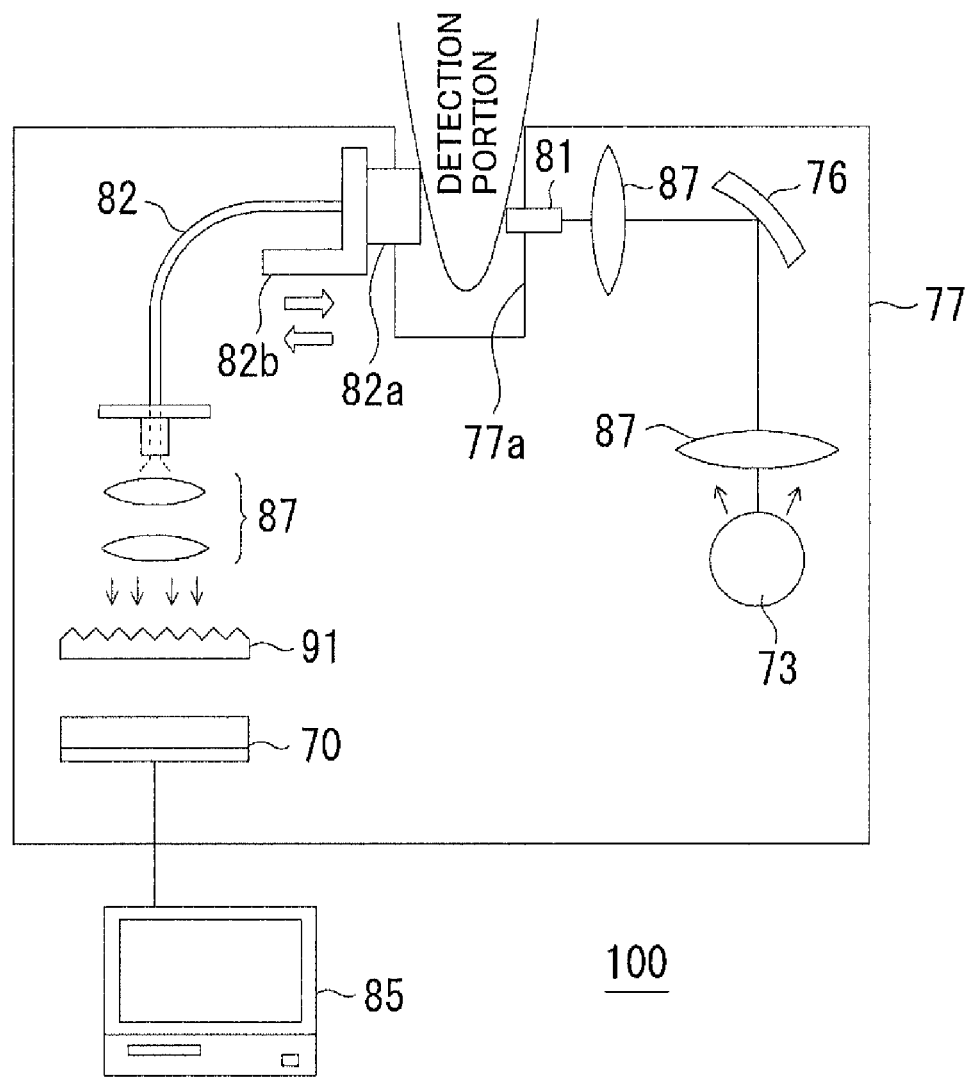
FIG. 16 is a view showing a biological component detection device (3) according to Embodiment 5 of the present invention.

Biological Component Detection Device (3)—Blood Sugar Level: Measurement by using Transmitted Light FIG. 16 is a view showing a biological component detection device 100 according to Embodiment 5 of the present invention. This biological component detection device 100 is characterized in that a biological object insertion trench 77a is provided in a part of a casing 77, and the blood sugar level is detected by using light transmitted through a biological object inserted into the biological object insertion trench 77a. It is assumed that a portion of the biological object to be inserted is a portion extending from the shoulder, that is, the portion is, for example, the arm or the palm. The biological object insertion trench 77a can have the largest size among the sizes of these portions. In particular, the biological object insertion trench 77a may be a trench that is especially for the earlap.

The path of the near-infrared light is as follows:

light source 73→condenser lens 87→reflecting mirror 76→condenser lens 87→irradiation optical fiber 81→detection portion→light-receiving end 82a→pressure-adjusting actuator 82b→information-carrying optical fiber 82→condenser lenses 87→diffraction grating 91→detection device 70 (refer to FIG. 8)

A lower portion of the little finger when the hand is open can transmit light without the light passing through the bone, and thus this is effective to measure the blood sugar level. There is no need for the target of the biological object insertion trench 77a to be particularly limited to a palm portion located in the lower portion of the little finger, and positioning may be performed using the pressure-adjusting actuator 82b or the like. With this structure, a patient can measure the blood sugar level easily with high accuracy by her/himself.

As in Embodiments 3 and 4, the light-receiving element array 50 in the detection device 70 can receive light up to a long-wavelength range of the near-infrared region and improves measurement accuracy. It is preferable to use a halogen lamp or the like as the light source. However, in this biological component detection device 100, a continuum light source or light-emitting diode (LED), which generates less heat, is preferably used as the light source.

EMBODIMENT 6

Figure 17:
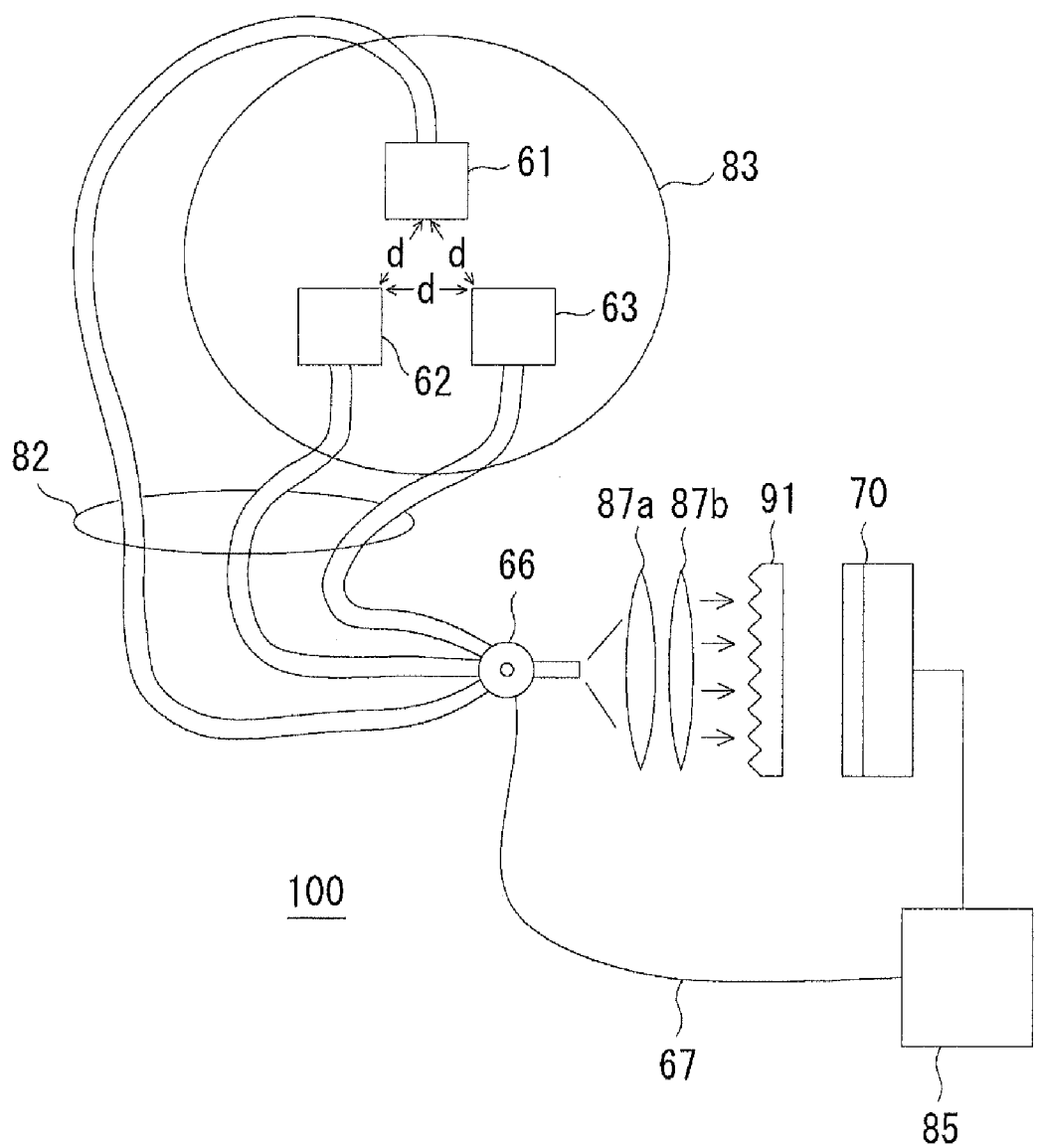
FIG. 17 is a view showing a biological component detection device (4) according to Embodiment 6 of the present invention.
Figure 18:
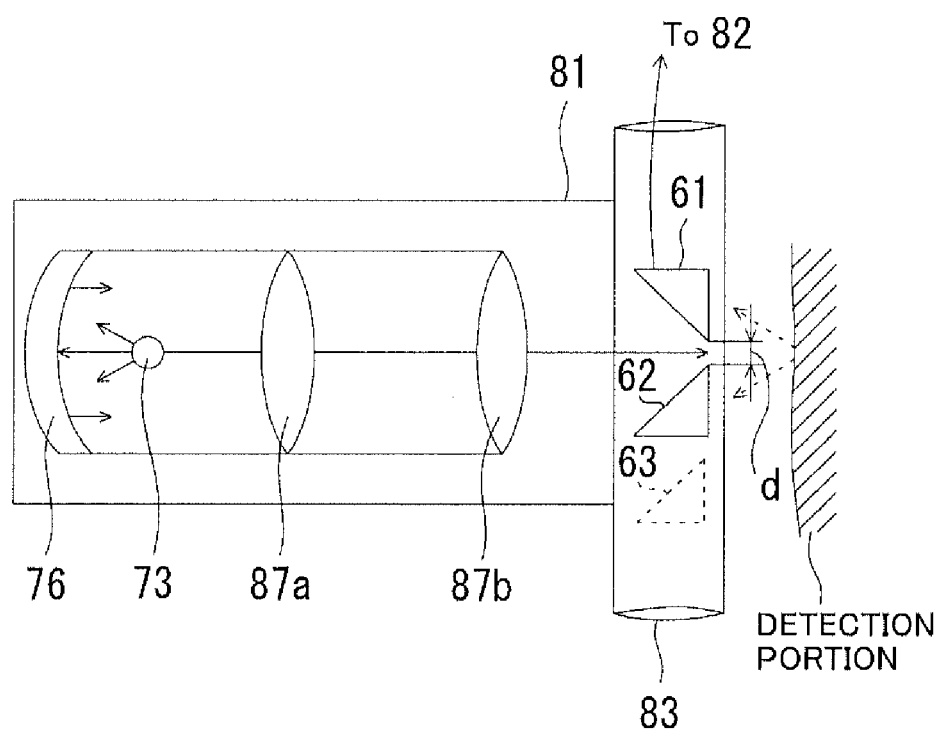
FIG. 18 is an enlarged view of a probe of the biological component detection device shown in FIG. 17.

Biological Component Detection Device (4)—Blood Sugar Level: Improvement in the Accuracy by Performing a Plurality of Samplings using a Single Probe FIG. 17 is a view showing a biological component detection device 100 according to Embodiment 6 of the present invention. FIG. 18 is an enlarged view of a probe of the biological component detection device 100 shown in FIG. 17. In this biological component detection device 100, a detection portion (skin) is irradiated with near-infrared light, and information is obtained from reflected light. In this case, as shown in FIG. 18, the irradiated light and the probe are each single, but three light-receiving ends 61, 62, and 63 are disposed in the probe 83. Near-infrared light components received in these three light-receiving ends 61, 62, and 63 propagate through separate information-carrying optical fibers 82. When light is spectrally separated in a diffraction grating 91 and received in a detection device 70 (reefer to FIG. 8), light components received in the light-receiving ends 61, 62, and 63 and propagating through the information-carrying optical fibers 82 are separately spectrally separated and received using a selecting switch 66. A feature in this embodiment lies in that a plurality of light-receiving ends are disposed in a single probe, and reflected light components are taken at a plurality of positions, spectrally separated, and analyzed. Prisms, optical fibers, or the like can be used as the light-receiving ends.

Near-infrared light irradiated on the skin diffuses in a surface layer portion in the skin, then goes to the outside, and is taken in the light-receiving ends. By taking light at a plurality of positions or by performing a plurality of samplings, the path of near-infrared light in the skin of the detection portion is determined not as a specific one path but as an averaged path. This averaging of the path in the surface layer portion of the skin can markedly improve the reliability of data of the blood sugar level. In order to reliably achieve the advantage of this plurality of samplings, a distance d between the light-receiving ends is preferably, for example, about 1 mm or more.

The biological component detection device 100 shown in FIG. 17 can show a spectrum in a wavelength from 1 μm to 3 μm for respective light components of the light-receiving ends 61, 62, and 63. In an operation unit (microcomputer) 85, with respect to light components from the respective light-receiving ends, the concentration of a biological component can be obtained by using a plurality of the same wavelengths or a plurality of different wavelengths for the light components. As for the biological component, not only the blood sugar level but also cholesterol, albumin, hemoglobin, bilirubin, or the like can be detected with high accuracy.

EMBODIMENT 7

Biological Component Detection Device (5)—Body Fat

Figure 19:
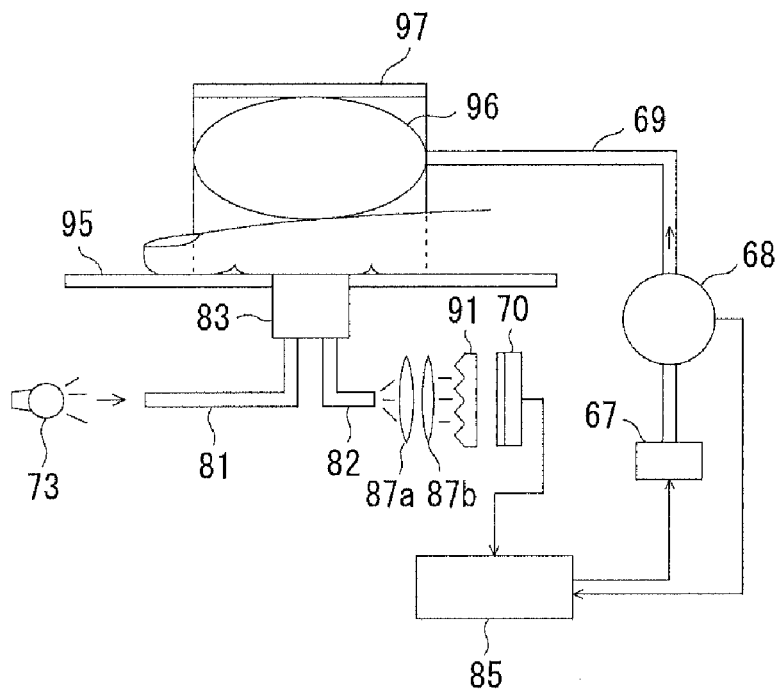
FIG. 19 is a view showing a biological component detection device (5) according to Embodiment 7 of the present invention.

FIG. 19 is a view showing a biological component detection device 100 according to Embodiment 7 of the present invention. In this embodiment, a biological component is body fat. Since body fat has a plurality of absorption bands in the near-infrared region, body fat can be detected by a near-infrared spectrum. In the detection of body fat, a pressure is applied. In FIG. 19, a probe 83 is fitted in a table 95, and a biological object (finger) is placed on the probe 83. An irradiation optical fiber 81 and an information-carrying optical fiber 82 are connected to the probe 83. A pressure is applied to the finger with an air bag 96. The air bag 96 is stowed in a housing 97, and air is charged and discharged through an air piping 69. A microcomputer 85 operates an air pump 69 as required on the basis of a pressure gauge 68 so that air is fed from the air piping 69 to the air bag 96. Thus, a pressure can be applied to the finger.

The path of the near-infrared light is as follows: light source 73→irradiation optical fiber 81→probe 83→finger→probe 83→information-carrying optical fiber 82→diffraction grating 91→detection device 70 (refer to FIG. 8)→microcomputer 85

The pressure applied to the finger can be known with the pressure gauge 68, and the proportion of body fat can be determined for each pressure. Hitherto, an absorption peak at 1.21 μm has been exclusively used in the detection of body fat using near-infrared light. As described above, by using the light-receiving element array 50 in the detection device 70 (refer to FIGS. 3 and 8), the range in which light can be received can be extended to a wavelength of 3 μm. Accordingly, the percent of body fat can be detected with higher accuracy using an absorption peak up to 3 μm in the longer-wavelength range.

EMBODIMENT 8

Biological Component Detection Device (6)—Detection of Collagen Distribution of Cornea Here, a description will be made of the usefulness of a biological component detection device according to the present invention for detecting the collagen distribution in a biological object, in particular, in the cornea of the eye, which is sensitive to light, though this detection is not performed to solve a specific problem. The cornea is mainly composed of collagen and a tissue fluid. This collagen is an important component in terms of beauty, and the absorption bands of collagen are mainly distributed in the range of 1 to 3 μm. Therefore, collagen is suitable for detection with the light-receiving element array 50 of the present invention shown in FIG. 3 or the imaging device 70 of the present invention shown in FIG. 8.

Figure 20:
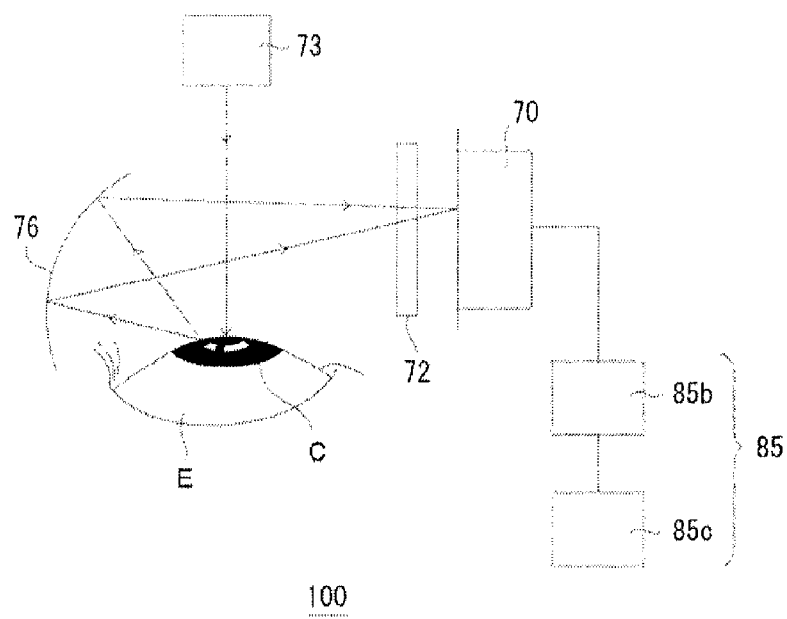
FIG. 20 is a view showing a biological component detection device (6) according to Embodiment 8 of the present invention.

FIG. 20 is a view showing a biological component detection device (device for forming an image of the collagen distribution of the eye) 100 according to Embodiment 8 of the present invention. Although the way in which the eye sees is not determined only by the cornea, it is important to know the state of the cornea.

As a concave mirror 76, a concave mirror having a high reflectivity to near-infrared light is preferably used. For example, a concave mirror composed of gold (Au) is used. The concave mirror 76 is disposed not in front of the eye but beside the eye so that light from the cornea is reflected to form an image of the cornea on an imaging device 70. A filter 72 preferably transmits light in the range of 1 to 3 μm that belongs to the absorption bands of collagen. A microcomputer 85b of a control unit 85 forms a collagen distribution image in the cornea C on the basis of output signals of pixels of the imaging device 70 and displays the image on a display device 85c. The imaging device 70 according to the present invention is preferably, for example, the imaging device 70 shown in FIG. 8. Since the dark current is low and the sensitivity is high to the long-wavelength side, a sharp collagen distribution image having a high S/N ratio can be obtained. Therefore, this collagen distribution image is useful for understanding the function of collagen in the eye, for example.

Figure 21:
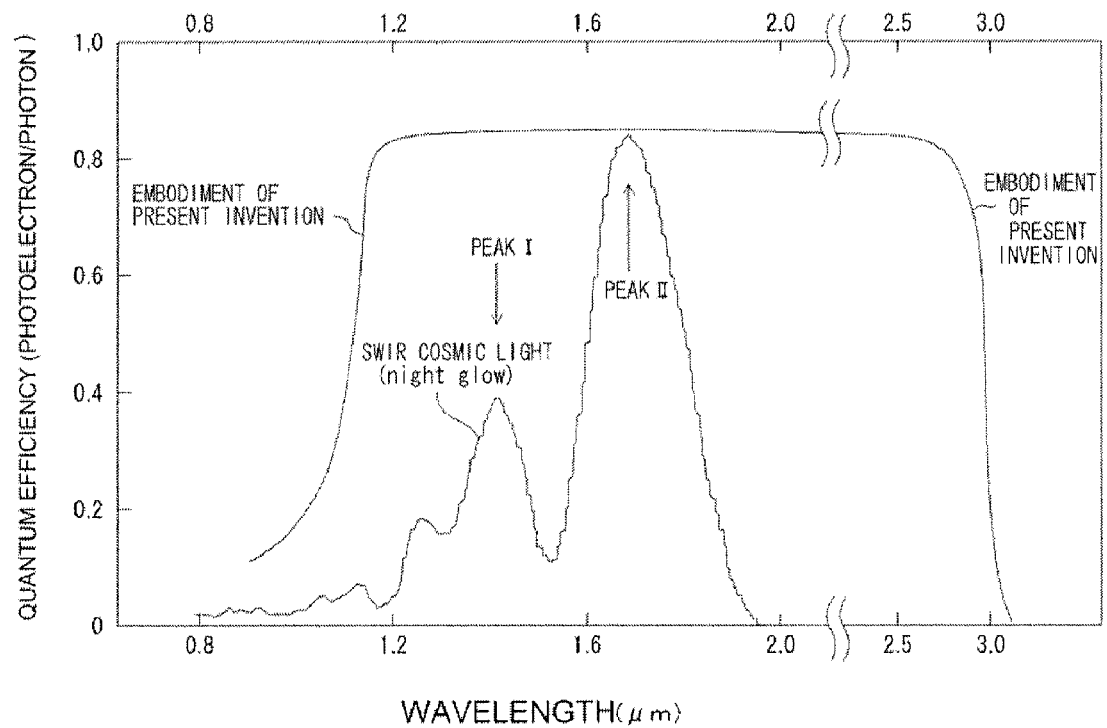
FIG. 21 is a graph showing SWIR cosmic light spectrum and a sensitivity distribution of a light-receiving element according to an embodiment of the present invention.

Since the eye very sensitively responses to light, it is preferable that a light source 73 be not used. FIG. 21 is a graph showing the intensity distribution of SWIR cosmic light. For example, a peak I of this SWIR cosmic light spectrum can be used as a light source. The wavelength of the peak I lies at about 1.4 μm, which is close to an absorption band of collagen. Accordingly, in FIG. 21, the light source 73 is removed and the SWIR cosmic light can be alternatively used. Alternatively, if an artificial light source 73 is used, the light may be limited to the near-infrared region and the peak value of the light may be, for example, double the peak intensity of the SWIR cosmic light. By using the SWIR cosmic light as a light source, eye-safe can be reliably realized. The reason why the SWIR cosmic light can be used or a light source having a low intensity level can be used as described above is that the dark current of the imaging device 70 according to the present invention can be reduced. That is, the reason is that a sharp image can be formed even by a weak signal.

EMBODIMENT 9

Biological Component Detection Device (7)—Detection of Collagen Distribution of Cornea in Corneal Corrective Surgery It is known that the cornea is evaporated using an ArF excimer laser to perform a precise corneal corrective surgery. Such a corneal corrective surgery is advantageous in that, for example, controllability of the amount of correction is good, the surgery is automated, the stability is good, infective side-effects after the surgery are small, and a decrease in the strength of the cornea is small. In the above corneal corrective surgery, the clinical test results regarding slight nearsightedness and medium nearsightedness are effective. On the other hand, when the number of times laser irradiation is performed on a central part of the cornea by an ArF excimer laser is increased, a biological fluid is significantly leached out onto the surface of the cornea, and evaporation of the cornea does not proceed. Accordingly, an intended amount of correction cannot be achieved for strong nearsightedness, resulting in a problem of the success rate of the surgery being decreased. In irradiation of an ArF excimer laser on the cornea, when nitrogen gas is sprayed in order to remove mushroom-shaped atomization generated from the surface of the cornea during its evaporation, the surface is dried, resulting in a problem of degradation of smoothing of the evaporation surface.

As described above, a damp or wet condition of the surface of the cornea during the surgery is an important factor that has an influence on the success or failure of the evaporation, and thus it is necessary to monitor the damp or wet condition of the surface of the cornea during the surgery. In evaporation of the cornea by irradiation of an ArF excimer laser, collagen mainly absorbs the laser and evaporates, and a tissue fluid, which accounts for about 80% of the cornea, is leached from the remaining cornea. Consequently, the composition of the portion after the leaching changes, and the absorption of the ArF excimer laser changes. The ArF excimer laser used in the evaporation of collagen is converted to vibration and rotation of molecules of collagen, resulting in an increase in the temperature. Consequently, infrared light having an intensity in proportion to the fourth power of the temperature is emitted. It has been proposed that a damp or wet condition of the cornea can be detected by monitoring this infrared light (Patent Document 7). In this method, only a single waveform of the infrared light corresponds to the entire part of one cornea C, and thus only information about an average damp or wet condition of the entire cornea is obtained. In reality, however, leaching of the tissue fluid separately occurs in the single cornea in the form of islands. Therefore, it is preferable to obtain information about the damp or wet condition at respective positions of the cornea.

By using the imaging device 70 or the light-receiving element two-dimensional array 50 according to the present invention, information about the collagen concentration at respective positions of the cornea can be specifically obtained. It is possible to detect a transition of the collagen distribution over the entire cornea when leaching of the tissue fluid temporarily occurs during a surgery. It is obvious that such detection provides valuable information to the condition of the cornea. In this case, a pulse width of the pulse laser is on the order of 10 nanoseconds (ns), and it is important to detect the collagen distribution within several milliseconds (ms) to 1,000 ms thereafter. After an ArF excimer laser shot, mushroom-shaped atomization due to evaporation of the cornea is generated within about 10 ns. It is necessary to track and detect the collagen distribution on the surface of the cornea on the order of several milliseconds to several tens of milliseconds so that the influence of this atomization can be minimized.

Figure 22:
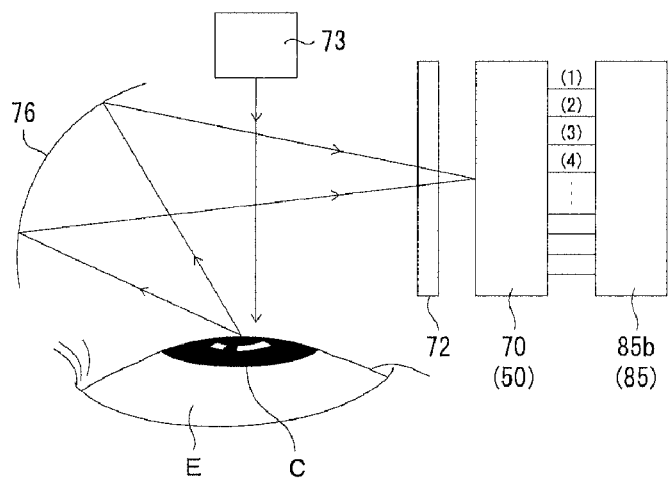
FIG. 22 is a view showing a biological component detection device (7) according to Embodiment 9 of the present invention.
Figure 23:
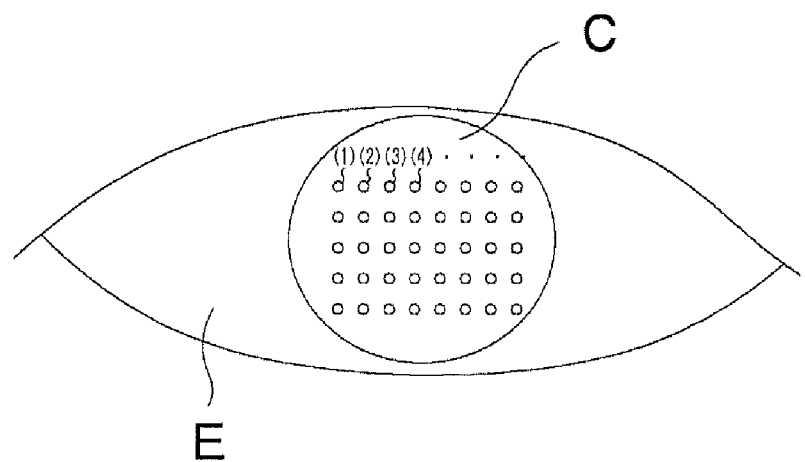
FIG. 23 is a view showing positions on the cornea at which collagen is detected.

FIGS. 22 and 23 are views illustrating a device configured to detect the collagen distribution of the cornea during a surgery according to Embodiment 9 of the present invention. A light source 73 is disposed so as not to overlap with an output portion (not shown) of an ArF excimer laser. In FIG. 22, an optical system is configured to form an image of the cornea on an imaging device 70 or a light-receiving element two-dimensional array 50. At a position of the cornea containing a large amount of collagen, an output voltage of a pixel or a light-receiving element is low (dark), and at a position of the cornea containing a small amount of collagen, the output voltage thereof is high (bright). Immediately after an ArF excimer laser shot, a waveform (temporal transition) of the output voltage of each pixel of the imaging device 70 or the light-receiving element two-dimensional array 50 is input to a processor 85b included in a control unit 85 and stored. The pixels of the imaging device 70 or light-receiving elements 10 of the two-dimensional array are assigned positions of the cornea C that are divided into small portions, as shown in FIG. 23.

The imaging device 70 according to the present invention can form pixels at a density that is more than sufficient to medically know the collagen distribution of respective positions of the cornea. In addition, crosstalk between adjacent pixels is small and a dark current can also be significantly decreased. Furthermore, as described above, by forming a diffusion concentration distribution control layer composed of InGaAs, the response time can be reduced. Accordingly, an output voltage waveform can be obtained with a high tracking capability and high accuracy in each of the pixels. All such waveforms of the pixels are collected, and the collagen distribution concentrations are plotted on a map of the cornea. Thus, it is possible to determine a leaching state of the entire cornea immediately after an ArF excimer laser shot.

EMBODIMENT 10

Biological Component Detection Device (8)—Image of Collagen Distribution of Face An image of the collagen distribution of the face is important in terms of beauty. When wrinkles are formed at an end of the lip or a tail of the eye, it is believed that the collagen concentration is low (Patent Document 6). A high collagen concentration and a wrinkle-free supple skin may have a high correlation. The configuration of an imaging device 70 of this embodiment is the same as that of Embodiment 8 or 9, and thus the imaging device 70 is not shown in the figure.

A sharp image of the collagen distribution of the face can be obtained by using the imaging device 70 according to the present invention. Furthermore, as described above, acquiring an image of the collagen distribution of the face involves a problem of eye-safe. According to the imaging device 70 of the present invention, a sharp image can be obtained even with a weak signal, and thus the SWIR cosmic light can be used without using a light source. Alternatively, even in the case where a light source is used, a light source having a low emission intensity can be used. Therefore, it is easy to overcome the problem of eye-safe.

EXAMPLE

Example Regarding Structure of Semiconductor Light-Receiving Element Array

Figure 24:
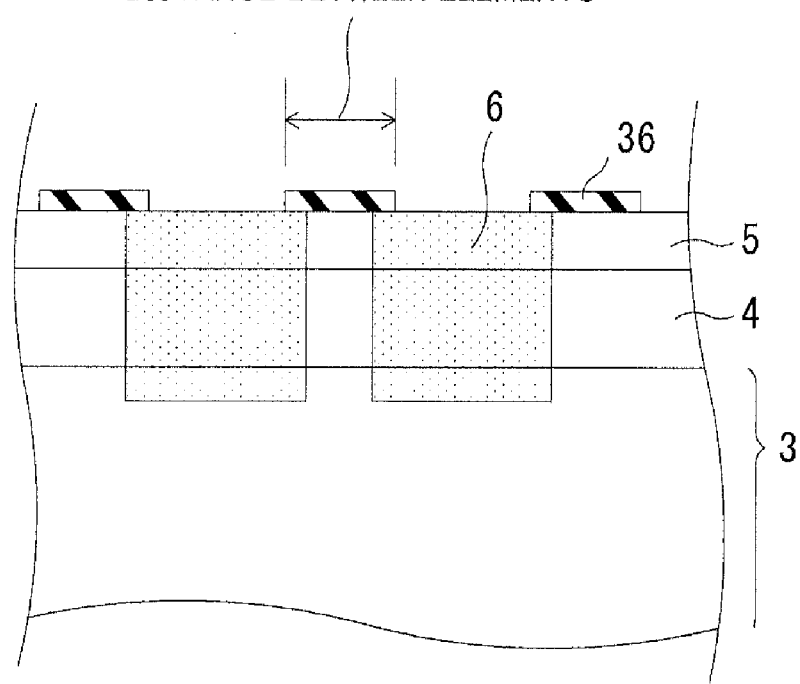
FIG. 24 is a partial cross-sectional view of a light-receiving element array used in Example.

To which degree the pixel pitch or the distance between elements of the light-receiving element array of the present invention can be decreased was examined by way of Example using the light-receiving element array shown in FIG. 24. The distance between light-receiving elements or the pixel pitch is the width of a masking portion of a SiN selective diffusion mask pattern 36, as shown in FIG. 24. After selective diffusion of Zn, a p-side electrode 11 made of AuZn and an n-side electrode 12 made of AuGeNi were formed. In the case of FIG. 3, since an Fe-doped semi-insulating substrate is used as the InP substrate 1, the n-side electrode 12 is provided on the buffer layer 2 containing an impurity at a high concentration. In the case where the n-type InP substrate is used as shown in FIG. 1, the n-side electrode may be provided on the reverse face of the substrate, or the n-side electrode may be provided on an n-type semiconductor layer (e.g., buffer layer 2) adjacent to the substrate on the top surface side of the substrate. In this Example, a reverse bias voltage of 5 V was applied between the p-side electrode 11 and the n-side electrode 12 of the light-receiving element array shown in FIG. 3 to measure the dark current. Light-receiving element arrays having two types of the thickness of the InP window layer 5 of 0.6 μm and 1.6 μm and seven types of the distance between elements in the range of 3 to 20 μm were produced to measure the dark current. The thickness of the diffusion concentration distribution control layer 4 was 1 μm.

Figure 25:
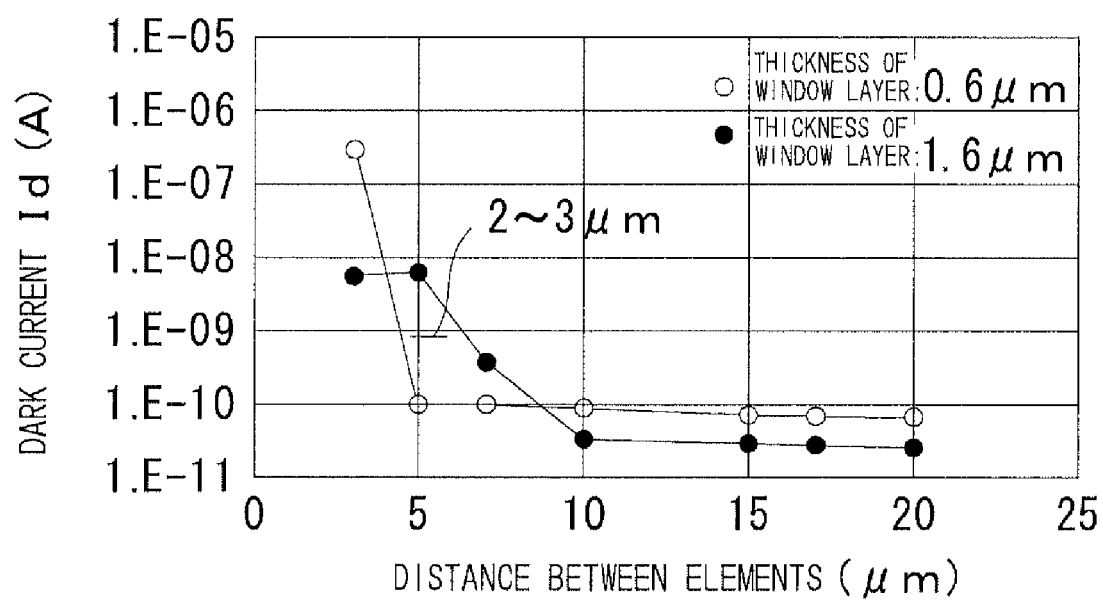
FIG. 25 is a graph showing a relationship between the distance between elements and a dark current measured in Example.

The results are shown in FIG. 25. Referring to FIG. 25, in the case where the InP window layer 5 has a small thickness of 0.6 μm, even when the distance between elements or the pixel pitch is reduced to 5 μm, the dark current can be suppressed to $1\times10^{-10}$ A (ampere). In the case where the InP window layer 5 has a thickness of 1.6 μm, diffusion of Zn expands in the lateral direction as described above. Therefore, unless the distance between elements exceeds 7 μm, the dark current cannot be suppressed to $1\times10^{-10}$ A. However, in this Example, it was confirmed that the distance between elements could be reduced to 5 μm by reducing the thickness of the InP window layer 5 to 0.6 μm and disposing the diffusion concentration distribution control layer.

Figure 26:
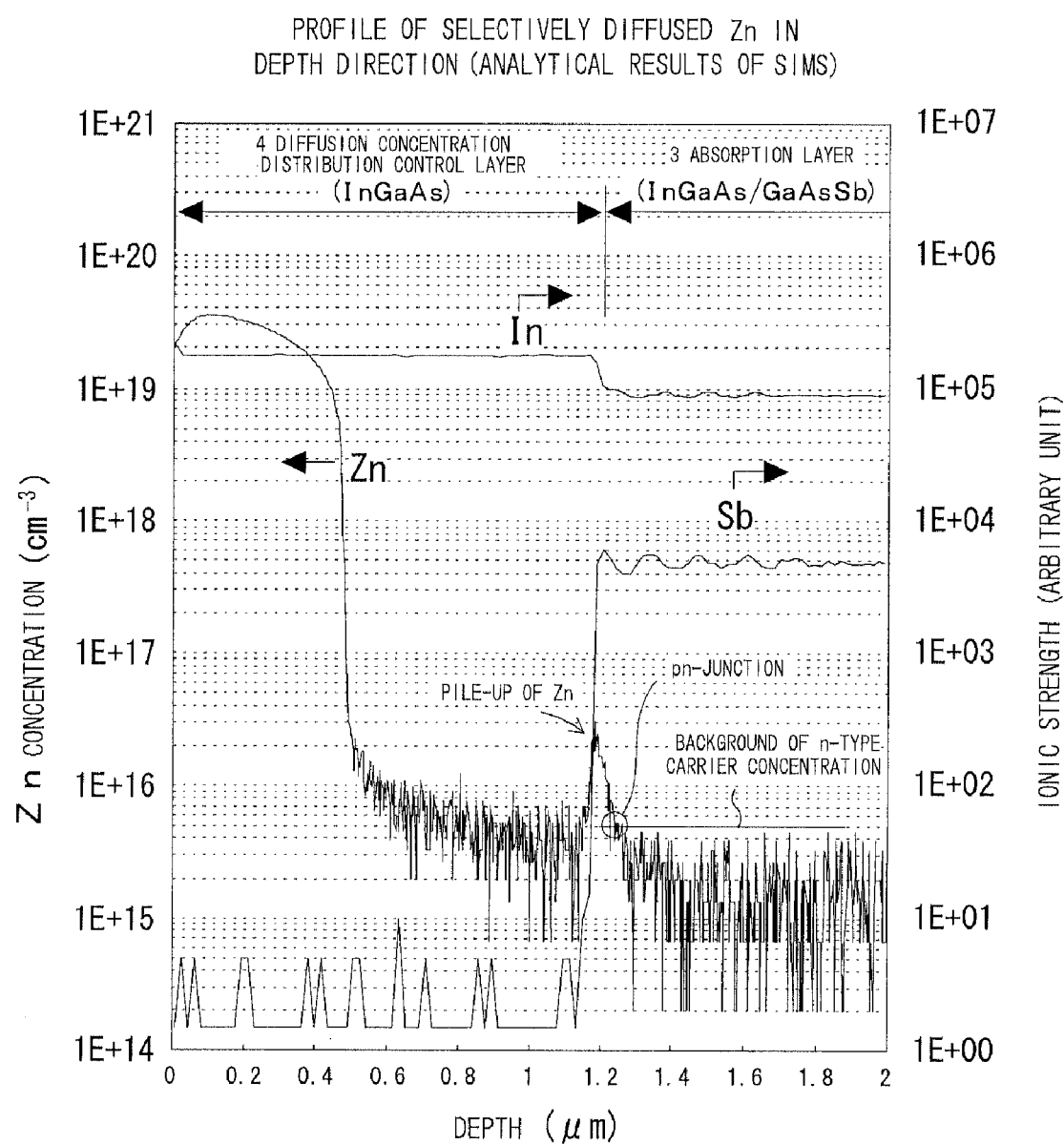
FIG. 26 is a graph showing a concentration distribution of Zn in the depth direction in Example.

The function of the diffusion concentration distribution control layer 4 was examined by analyzing a concentration distribution of Zn in the depth direction by SIMS. FIG. 26 shows the concentration distribution of Zn in the depth direction. Referring to FIG. 26, at the boundary face between the InGaAs diffusion concentration distribution control layer 4 and the absorption layer 3, the peak value of pile-up of Zn is suppressed to $5\times10^{16}$ cm$^{-3}$ or less. Accordingly, in a pn-junction formed at a crossing position (a circle mark in the figure) of the background of the n-type carrier concentration of the absorption layer 3 and the Zn concentration, the Zn concentration can be reliably reduced, and degradation of the crystal quality or the like can be prevented. In addition, by disposing this diffusion concentration distribution control layer 4, it becomes possible for the multiple quantum well structure of the absorption layer to achieve the original function thereof.

Embodiments and Example of the present invention have been described above. The embodiments and Example of the present invention disclosed above are only illustrative, and the scope of the present invention is not limited to these embodiments of the invention. It is to be understood that the scope of the present invention is defined by the description of Claims and includes equivalence of the description in Claims and all modifications within the scope of Claims.

INDUSTRIAL APPLICABILITY

According to the present invention, an examination with high accuracy can be easily performed by an outstanding improvement of the performance of InP-based PDs, as compared with existing devices. Thus, the present invention can significantly contribute to the field of health and beauty.

What is claimed is:
1. A biological component detection device for detecting a component of a biological object using light in the near-infrared region, comprising
a light-receiving element composed of III-V group semiconductor, that receives light in the near-infrared region,
wherein, the light-receiving element including an absorption layer formed on an InP substrate and having a multiple quantum well structure,
the absorption layer having a bandgap wavelength of 1.8 μm or more and 3 μm or less,
a diffusion concentration distribution control layer made of III-V group semiconductor is disposed in contact with the absorption layer on a surface side of the absorption layer, the surface side being opposite to the InP substrate,
the diffusion concentration distribution control layer having a bandgap smaller than that of InP,
wherein, in the light-receiving element, a pn-junction is formed by selectively diffusing an impurity element through the diffusion concentration distribution control layer so as to reach the absorption layer,
the concentration of the impurity element in the absorption layer is $5\times10^{16}$/cm$^3$ or less, the diffusion concentration distribution control layer has an n-type impurity concentration of $2 \times 10^{15}/cm^3$ or less before the diffusion, the diffusion concentration distribution control layer having a portion adjacent to the absorption layer, the portion having a low impurity concentration, and the detection is performed by receiving, with the light-receiving element, light having at least one wavelength of 3 μm or less, the light constituting light transmitted through or reflected from the biological object.

2. The biological component detection device according to claim 1, wherein the diffusion concentration distribution control layer has a first region located adjacent to a surface of the diffusion concentration distribution control layer opposite the surface in contact with the absorption layer, the concentration of the impurity element in the first region being about $1 \times 10^{18}/cm^3$ or more, a second region located adjacent to the absorption layer, the concentration of the impurity element in the second region being $2 \times 10^{16}/cm^3$ or less, and a third region located between the first region and the second region, the third region having a smaller thickness than those of the first and second regions, and the concentration of the impurity element in the third region being more than $2 \times 10^{16}/cm^3$ and less than $1 \times 10^{18}/cm^3$.

3. The biological component detection device according to claim 1, wherein the absorption layer has a type II quantum well structure.

4. The biological component detection device according to claim 3, wherein the absorption layer has a multiple quantum well structure composed of (InGaAs/GaAsSb) or a multiple quantum well structure composed of (GaInNAs (P, Sb)/GaAsSb).

5. The biological component detection device according to claim 1, wherein the InP substrate is an off-angle substrate which is tilted at 5° to 20° from (100) in the [111] direction or the [11-1] direction.

6. The biological component detection device according to claim 1, wherein the impurity element is zinc (Zn), and the diffusion concentration distribution control layer is composed of InGaAs.

7. The biological component detection device according to claim 1, further comprising an InP window layer disposed on the diffusion concentration distribution control layer.

8. The biological component detection device according to claim 7, wherein, in any two of the InP substrate, respective layers constituting the quantum well structure of the absorption layer, the diffusion concentration distribution control layer, and the InP window layer, a degree of lattice matching ($|\Delta a/a|$: where a represents a lattice constant and $\Delta a$ represents a difference in the lattice constant between the two) is 0.002 or less.

9. The biological component detection device according to claim 1, wherein a plurality of the light-receiving elements are one-dimensionally or two-dimensionally arrayed.

10. The biological component detection device according to claim 1, wherein a detection portion of the biological object is irradiated with light emitted from a supercontinuum light source (SC light source) or a light-emitting diode (LED), and light transmitted through or reflected from the detection portion is received.

11. The biological component detection device according to claim 1, further comprising an imaging device including a two-dimensional array of the light-receiving element, wherein a distribution image of a component contained in the biological object which is an examination target is formed with the imaging device.

12. The biological component detection device according to claim 1, wherein the biological object is irradiated with light in the wavelength region, and light reflected from the biological object or light transmitted through the biological object is received to detect at least one component selected from glucose, grape sugar, hemoglobin, cholesterol, albumin, active oxygen, fat, and collagen contained in the biological object.

13. The biological component detection device according to claim 12, further comprising a spectral separation unit configured to spectrally separate light; a plurality of the light-receiving elements or a light-receiving element array located in accordance with the spectrally separated wavelength; and a control unit configured to perform an operation on the basis of the results of light reception performed by the light-receiving elements or the light-receiving element array to calculate the concentration of the component of the biological object, the spectral separation unit being disposed on the irradiation side of the light of the detection portion or behind the detection portion when viewed from the irradiation side.

* * * * *